US009062245B2

(12) United States Patent
Silverstein et al.

(10) Patent No.: US 9,062,245 B2
(45) Date of Patent: Jun. 23, 2015

(54) LIQUID-RETAINING ELASTOMERIC COMPOSITIONS

(75) Inventors: Michael S. Silverstein, Zikhron-Yaakov (IL); Inna Gurevitch, Haifa (IL)

(73) Assignee: Technion Research & Development Foundation Limited, Haifa (IL)

( * ) Notice: Subject to any disclaimer, the term of this patent is extended or adjusted under 35 U.S.C. 154(b) by 617 days.

(21) Appl. No.: 13/369,362

(22) Filed: Feb. 9, 2012

(65) Prior Publication Data

US 2012/0201806 A1 Aug. 9, 2012

Related U.S. Application Data

(60) Provisional application No. 61/440,882, filed on Feb. 9, 2011.

(51) Int. Cl.

*C08J 9/00* (2006.01)
*C08J 9/35* (2006.01)
*C09K 15/06* (2006.01)
*B82Y 30/00* (2011.01)
*H01F 1/28* (2006.01)
*H01F 1/375* (2006.01)

(52) U.S. Cl.

CPC ................. *C09K 15/06* (2013.01); *B82Y 30/00* (2013.01); *H01F 1/28* (2013.01); *H01F 1/375* (2013.01)

(58) Field of Classification Search

CPC .......... B82Y 30/00; C09K 15/06; H01F 1/28; H01F 1/375; C08F 2220/1858; C08F 2230/085

USPC ...................... 521/61, 63, 64, 89, 91, 92, 149

See application file for complete search history.

(56) References Cited

U.S. PATENT DOCUMENTS 2,801,185 A 7/1957 Iler
4,455,205 A 6/1984 Olson et al.
4,478,876 A 10/1984 Chung
4,486,504 A 12/1984 Chung
4,491,508 A 1/1985 Olson et al.
4,522,958 A 6/1985 Das et al.
5,258,225 A 11/1993 Katsamberis
5,648,407 A 7/1997 Goetz et al.
6,147,131 A 11/2000 Mork et al.
6,204,298 B1 * 3/2001 DesMarais et al. ............. 521/64
6,353,037 B1 * 3/2002 Thunhorst et al. .............. 521/64
6,586,483 B2 7/2003 Kolb et al.
7,129,277 B2 10/2006 Baran, Jr.
7,189,768 B2 3/2007 Baran, Jr. et al.
7,507,780 B2 3/2009 Hagerty et al.
2003/0097103 A1 5/2003 Horney et al.
2009/0215913 A1 8/2009 Thies et al.
2010/0261803 A1 * 10/2010 Bismarck et al. ............... 521/76

FOREIGN PATENT DOCUMENTS

WO WO 02/08321 1/2002
WO WO 2009/013500 1/2009

OTHER PUBLICATIONS

Barbetta et al. "High Internal Phase Emulsions (HIPEs) Containing Divinylbenzene and 4-Venylbenzyl Chloride and the Morphology of the Resulting PolyHIPE Materials", Chemical Communications, p. 221-222, 2000.

Colver et al. "Cellular Polymer Monoliths Made Via Pickering High Internal Phase Emulsions", Chemical Materials, 19: 1537-1539, 2007.

Gurevitch et al. "Polymerized Pickering HIPEs: Effects of Synthesis Parameters on Porous Structure", Journal of Polymer Science, Part A: Polymer Chemistry, 48: 1516-1525, 2010.

Ikem et al. "High Internal Phase Emulsions Stabilized Solely by Functionalized Silica Particles", Angewandte Chemie, International Edition, 47: 8277-8279, 2008.

Menner et al. "High Internal Phase Emulsion Templates Solely Stabilised by Functionalised Titania Nanoparticles", Chemical Communications, p. 4274-4276, 2007.

Menner et al. "Particle-Stabilized Surfactant-Free Medium Internal Phase Emulsions as Templates for Porous Nanocomposite Materials: Poly-Pickering-Foams", Langmuir, 23: 2398-2403, 2007.

Zhang et al. "PMMA Based Foams Made Via Surfactant-Free High Internal Phase Emulsion Templates", Chemical Communications, p. 2217-2219, 2009.

* cited by examiner

*Primary Examiner* — Irina S Zemel

(57) ABSTRACT

Disclosed are compositions-of-matter composed of a continuous elastomeric matrix and a liquid; the matrix entrapping the liquid therein in the form of closed-cell droplets dispersed throughout the matrix. The disclosed compositions-of-matter are characterized by a low tensile/compressive modulus and are capable of retaining the liquid for exceedingly long periods of time. Further disclosed are processes for forming the compositions-of-matter and uses thereof.

34 Claims, 7 Drawing Sheets
(5 of 7 Drawing Sheet(s) Filed in Color)

FIG. 6A
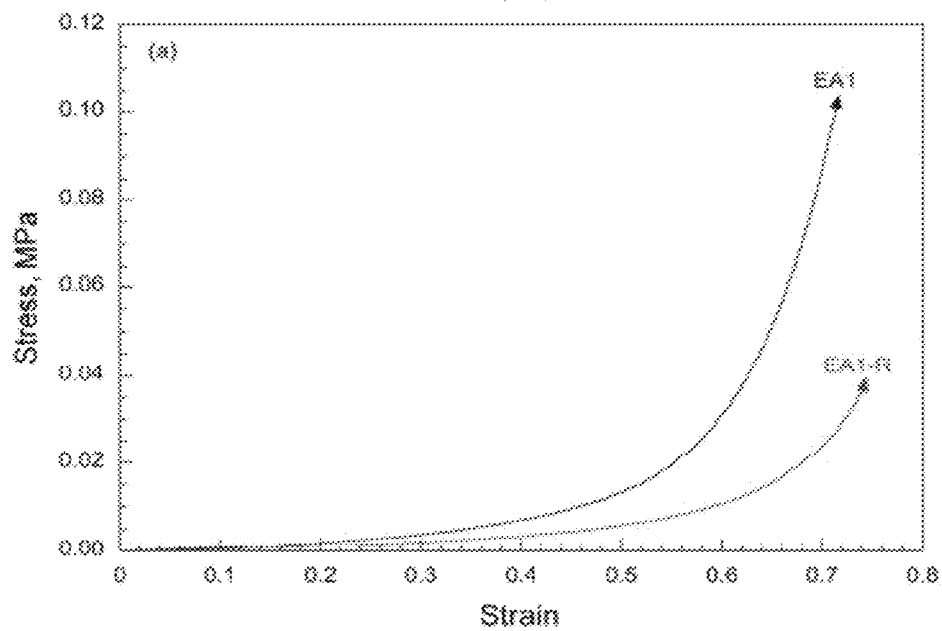
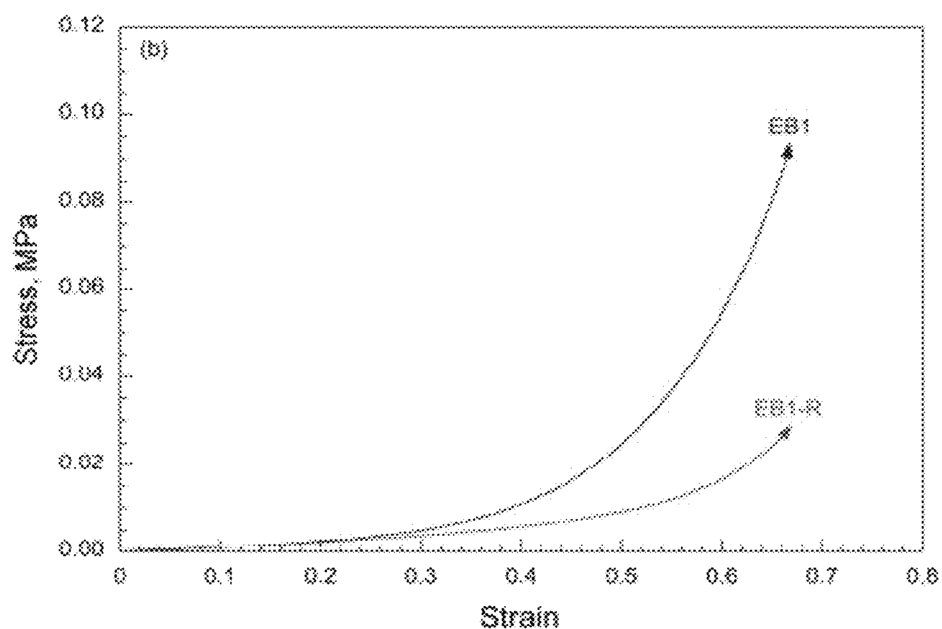
FIG. 6B

LIQUID-RETAINING ELASTOMERIC COMPOSITIONS

RELATED APPLICATIONS

This application claims the benefit of priority under 35 USC §119(e) of U.S. Provisional Patent Application No. 61/440,882 filed Feb. 9, 2011, the contents of which are incorporated herein by reference in their entirety.

FIELD AND BACKGROUND OF THE INVENTION

The present invention, in some embodiments thereof, relates to polymeric material science and, more particularly, but not exclusively, to HIPE-derived liquid-retaining elastomeric compositions.

High internal phase emulsions (HIPEs) are typically formed from two immiscible liquids, typically being water as a major dispersed or internal phase, and a highly hydrophobic liquid as a minor continuous or external phase, in the presence of a surfactant which is insoluble in the internal phase. The amount of surfactant needed to stabilize a major phase dispersed within a minor phase may reach up to 30% of the weight of the minor phase. HIPEs can also be stabilized through the formation of Pickering emulsions, as described below.

PolyHIPEs are highly porous polymers synthesized by polymerization of monomers within the external phase of HIPEs with internal phase volumes that are typically greater than 74% by volume of the emulsion. Most polyHIPEs are based on the co-polymerization of hydrophobic monomers and crosslinking co-monomers within the continuous phase of water-in-oil (w/o) HIPEs, followed by the removal of the internal phase, thereby producing a porous air-filled polymer.

A variety of polyHIPEs and polyHIPE-based materials have been synthesized and reported in the art. The porous morphology and properties of a polyHIPE was found to depend, among other factors, on the type and amount of the HIPE-stabilizing amphiphilic surfactant. Such surfactants are often difficult and/or costly to remove. These disadvantages become more acute for polyHIPEs where unusually large quantities of surfactant are needed, hence displacing the surfactants in HIPEs can prove advantageous, especially for polyHIPE syntheses.

High internal phase emulsions stabilized by surfactants and polyHIPEs made therefrom are disclosed, for example, in U.S. Pat. No. 6,147,131, which teaches porous polymeric materials (foams) made from HIPEs which include water-in-oil high internal phase emulsions having at least 70% of an internal aqueous phase and less than 30% of an external oil phase, wherein the oil phase comprises a vinyl polymerizable monomer and a surfactant effective to stabilize the emulsion, and wherein the surfactants are oil soluble and include an oxyalkylene component.

A Pickering emulsion (named after S.U. Pickering who first described the phenomenon in 1907) is a surfactant-free emulsion stabilized by micro- or nano-scaled solid particles that preferentially migrate to the interface between the two liquid phases. The aforementioned standard amphiphilic surfactants reduce the oil-water interfacial tension. The solid particles of a Pickering emulsion form rigid shells that surround polyhedral or spheroidal droplets of the dispersed phase and prevent coalescence thereof. The particles' shape and size, inter-particle interactions, and the wetting properties of the particles with respect to the liquid phases affect its ability to stabilize HIPEs. The stability of Pickering emulsions based on inorganic particles can be enhanced by chemically modifying the particles' surface with organic moieties that increase their tendency to migrate to the interface, and determines their ability to stabilize oil-in-water (o/w) or water-in-oil (w/o) emulsions.

Several different chemical surface modification methodologies, including silane modification, have been used to change the hydrophilic nature of the surface of silica nanoparticles such that they are able to stabilize Pickering emulsions. Silane coupling agents are commonly used to enhance fiber/matrix adhesion in polymer composites. Alkoxysilanes and chlorosilanes contain groups that bind covalently with silica through reaction with the hydroxyl groups on its surface. These silanes also contain hydrophobic organic groups that decrease surface hydrophilicity. Silane-modification thus enhances the amphiphilic character of the particles' surface, making it more suitable for Pickering emulsions and the corresponding HIPE stabilization. The extent of silica surface reaction with methyldichlorosilane was demonstrated to affect the degree of hydrophobicity and to determine whether it would stabilize an o/w or a w/o Pickering emulsion. In addition to controlling surface hydrophobicity, a silane that bears a vinyl group as part of the chemical surface modification can act as a monomer during a co-polymerization reaction.

Pickering HIPEs containing up to 92% internal phase, stabilized with 1-5% by weight of titania and silica nanoparticles, whose surfaces were modified with oleic acid, have been reported [Menner, A. et al., *Chemical Communications,* 2007, 4274-4276; and Ikem, V. O. et al., *Angewandte Chemie International Edition,* 2008, 47, 8277-8279]. Similarly, partially oxidized carbon nanotubes were used to stabilize HIPEs containing up to 60% internal phase [Menner, A. et al., *Langmuir,* 2007, 23, 2398-2403] and poly(methyl methacrylate) microgel particles were used to stabilize HIPEs containing 50% internal phase [Colver, P. J.; Bon, S. A. F., *Chemistry of Materials,* 2007, 19, 1537-1539].

Thus, the advantages of using Pickering HIPEs with a relatively small amount of nanoparticles for forming polyHIPEs, include eliminating the need for standard surfactants, eliminating the need for procedures to remove such surfactants, and eliminating the problems associated with residual and leachable surfactants. Most of the polyHIPEs synthesized from such Pickering HIPEs exhibited relatively large voids (300 to 400 μm in diameter). Smaller voids of about 50 μm in diameter were observed when poly(styrene/methyl methacrylate/acrylic acid) particles were used to stabilize Pickering HIPE [Zhang, S.; Chen, J., *Chemical Communications,* 2009, 2217-2219]. PolyHIPEs from Pickering HIPEs do not usually exhibit the highly interconnected porous structures typical of conventional polyHIPEs but rather exhibit a somewhat interconnected structure.

U.S. Pat. No. 6,353,037 and WO 2002/008321 teach methods for making foams which include functionalized metal oxide nanoparticles by photo- or thermo-polymerizing emulsions comprising a reactive external phase and an immiscible internal phase. Although mentioning closed-cell structures, the polymeric foams disclosed in these documents are predominantly open-celled structures, wherein most or all of the cells are in unobstructed communication with adjoining cells. "Open-celled structures" are foams wherein the majority of adjoining cells are in open communication with each other; an open-cell foam includes foams made from co-continuous emulsions in which the cell structure is not clearly defined, but there are interconnected channels creating at least one open pathway through the foam. Hence, the cells in the substantially open-celled foam structures disclosed in this document have intercellular windows that are typically large enough to permit fluid transfer from one cell to another within the foam structure. After these foams have been polymerized, the residual immiscible internal phase fluid can be removed from the foam structure by vacuum drying, freeze drying, squeeze drying, microwave drying, drying in a thermal oven, drying with infrared lights, or a combination of these techniques.

Open-cell polyHIPE structures are demonstrated and presented photographically in a study of HIPEs containing divinylbenzene and 4-vinylbenzyl chloride [Barbetta, A. et al., *Chem. Commun.,* 2000, 221-222].

WO 2009/013500 teaches particle-stabilized high internal phase emulsions (Pickering HIPEs) comprising an internal phase, a continuous phase and particles comprising a core and a coating, wherein the wettability of the core is modulated by the coating of the particles. In the poly-Pickering-foams of WO 2009/013500, thin polymer films are formed in the area of contact points between neighboring internal-phase droplets, which rupture during the vacuum drying process and lead to a partially open porous foam structure of poly-Pickering-HIPEs. Hence, the thin polymer films which surround the droplets in the poly-Pickering-HIPEs disclosed in this document are relatively stable while the foam is wet, but as they are put under stress by the mechanical forces arising during the vacuum drying, some are forced to rupture, giving rise to some degree of interconnectivity to neighboring droplets, now pores or voids, and allows for the complete removal of the trapped internal aqueous phase.

In previous research, the present inventors investigated the synthesis of rubbery crosslinked polyacrylate materials based on Pickering HIPEs that were stabilized using silane-modified silica nanoparticles [Gurevitch, I.; Silverstein, M. S., *J. Polym. Sci. A: Polym. Chem.,* 2010, 48, 1516-1525]. This publication describes the open-celled, interconnected porous structure and the effects of the synthesis parameters on this structure.

Additional prior art documents include U.S. Patent Application Nos. 20090215913 and 20030097103.

SUMMARY OF THE INVENTION

The present invention is directed at a novel composition-of-matter and uses thereof, wherein the composition-of-matter combines substances (a polymer and a solution), states of aggregation (liquid and solid), which together give rise to a unique set of mechanical characteristics, as presented hereinbelow.

Hence, according to an aspect of embodiments of the invention presented herein, there is provided a composition-of-matter which includes a continuous elastomeric matrix and a liquid dispersed in the matrix in a form of a plurality of droplets, the elastomeric matrix entrapping the liquid in the droplets, the composition-of-matter being characterized by a compressive modulus of less than 600 MPa and by a mass loss $t_{1/2}$ greater than 10 days.

In some embodiments, the matrix has a closed-cell microstructure.

In some embodiments, the droplets are substantially polyhedral or spheroidal, exhibiting an average diameter of 10 nm to 500 μm.

In some embodiments, the wall separating the droplets has a thickness of 10 nm to 500 μm.

In some embodiments, the liquid is a solution which includes at least one solute.

In some embodiments, the solute is an active agent selected from the group consisting of a drug, an antibiotic agent, a polypeptide, an antibody, a catalyst, an anticorrosion agent, a fire retardant, a sealing agent, an adhesive agent, a colorant, an odoriferous agent, a lubricant and any combination thereof.

According to another aspect of embodiments of the invention presented herein, there is provided a process of preparing the composition-of-matter presented herein, which is effected by subjecting a high internal phase emulsion (HIPE) having an internal phase and a polymerizable external phase to polymerization of the polymerizable external phase, whereas the polymerization is initiated and effected substantially at an interface between the polymerizable external phase and the internal phase.

In some embodiments, the internal phase is an aqueous internal phase and the polymerizable external phase is an organic polymerizable external phase.

In some embodiments, the mass ratio of the organic polymerizable external phase to the aqueous internal phase in the HIPE ranges from 0.05 to 0.67.

In some embodiments, the aqueous internal phase and/or the organic polymerizable external phase includes an emulsion stabilizer.

In some embodiments, the emulsion stabilizer is selected from the group consisting of an organic surfactant, a polyoxyethylene glycol alkyl ether, a Span, a Hypermer, a Tween, a Triton, sodium dodecyl sulfate (SDS), sodium lauryl sulfate (SLS), a block copolymer, PEO-PPO-PEO, an inorganic surfactant, a polyphosphate, a plurality of modified or unmodified particles, a plurality of modified or unmodified metal oxide or semi-metal oxide particles or nanoparticles, a plurality of modified or unmodified silica particles or nanoparticles, a plurality of modified or unmodified titania particles or nanoparticles, a plurality of modified or unmodified zirconia particles or nanoparticles, a plurality of modified or unmodified alumina particles or nanoparticles, a plurality of modified or unmodified carbon black particles or nanoparticles, a plurality of modified or unmodified carbon nanotubes, and any combination thereof.

In some embodiments, the emulsion stabilizer is modified silica nanoparticles.

In some embodiments, the concentration of the modified silica nanoparticles ranges from 0.01% to 10% of the total weight of the organic polymerizable external phase.

In some embodiments, the modified silica nanoparticles have a plurality of polymerizable moieties attached thereon.

In some embodiments, the content of the polymerizable moiety on the modified silica nanoparticles ranges from 0.5 mmol to 10 mmol per 1 gram of modified silica nanoparticles.

In some embodiments, the modified silica nanoparticles having the plurality of polymerizable moieties attached thereon have a plurality of initiation moieties attached thereon.

In some embodiments, the content of the initiation moiety on the modified silica nanoparticles ranges from 0.5 mmol to 10 mmol per 1 gram of modified silica nanoparticles.

In some embodiments, the aqueous internal phase further includes a water-soluble initiation agent.

In some embodiments, the water-soluble initiation agent is selected from the group consisting of a water-soluble peroxide, a water-soluble persulfate, potassium persulfate (KPS) and ammonium persulfate (APS).

In some embodiments, the initiation moiety is an AGET-ATRP initiator.

In some embodiments, the aqueous internal phase further includes a catalyst system, as defined herein, and a reducing agent, and optionally can further include a ligand.

In some embodiments, the AGET-ATRP initiator moiety is p-chloromethyl phenyltrimethoxysilane, the catalyst system includes $CuBr_2$ (as a catalyst), and 2,2-bipyridine (as a ligand), and the reducing agent is ascorbic acid.

In some embodiments, the organic polymerizable external phase is an unpolymerized mixture which includes at least one monomer characterized as forming a polymer having a tensile modulus of less than 600 MPa.

In some embodiments, the monomer is selected from the group consisting of an acrylate, a methacrylate and a diene.

In some embodiments, the acrylate is selected from the group consisting of 2-ethylhexyl acrylate (EHA), n-butyl acrylate (nBA), ethyl acrylate (EA) and hexyl acrylate (HA).

In some embodiments, the concentration of the monomer ranges from 90% to 99.9% of the total weight of the organic polymerizable external phase.

In some embodiments, the unpolymerized mixture further includes a reinforcing agent, a curing agent, a curing accelerator, a catalyst, a tackifier, a plasticizer, a flame retardant, a flow control agent, a filler, organic and inorganic microspheres, organic and inorganic microparticles, organic and inorganic nanoparticles, a conducting agent, a magnetic agent, electrically conductive particles, thermally conductive particles, fibers, an antistatic agent, a antioxidant, a anticorrosion agent, a UV absorber, a colorant and combination thereof.

According to another aspect of embodiments of the invention presented herein, the composition-of-matter presented herein is prepared by the process presented herein.

In some embodiments, the composition-of-matter presented herein is used in forming an article-of-manufacture.

According to another aspect of embodiments of the invention presented herein, there is provided an article-of-manufacturing which includes the composition-of-matter presented herein.

In some embodiments, the composition-of-matter and/or the article-of-manufacturing presented herein, is selected from the group consisting of an energy absorption and dissipation article, a vibration absorption article, a noise absorption article, a cushioning article, a thermal insulating article, an impact protection article, dampening material, moisture and humidity control material, fire resistant material and any combination thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying figures. With specific reference now to the figures in detail, it is stressed that the particulars shown are by way of example and for purposes of illustrative discussion of embodiments of the invention. In this regard, the description taken with the figures makes apparent to those skilled in the art how embodiments of the invention may be practiced.

In the drawings:

Figure 1:
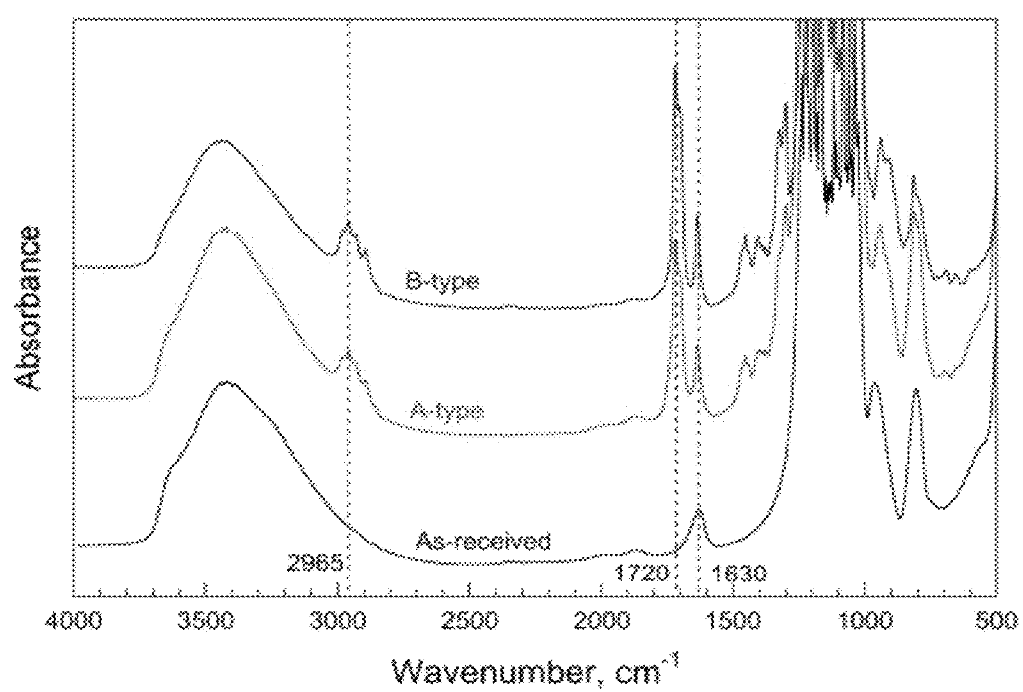
Figure 2:
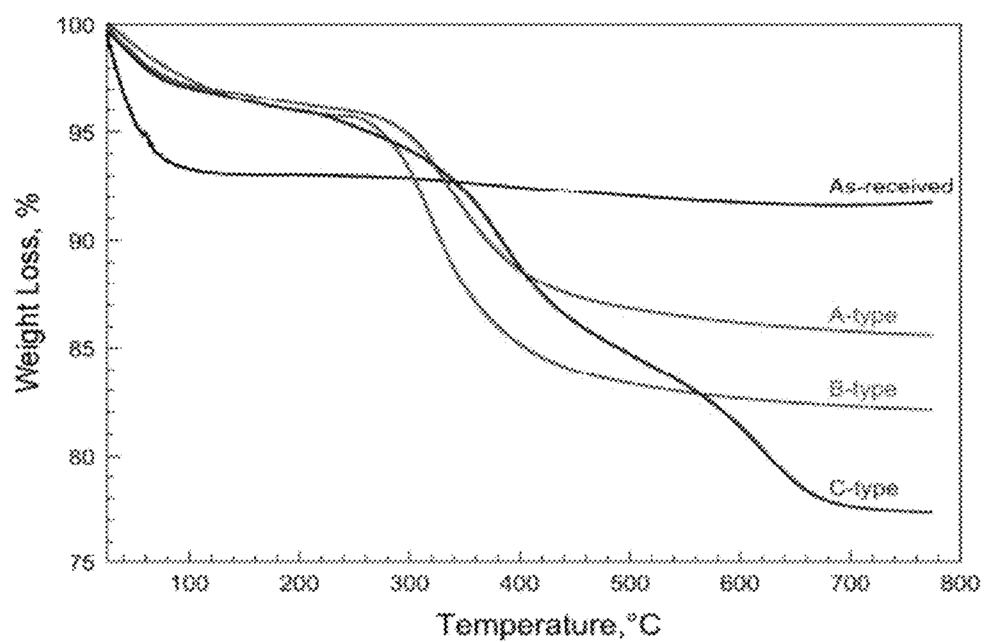
Figure 4A:
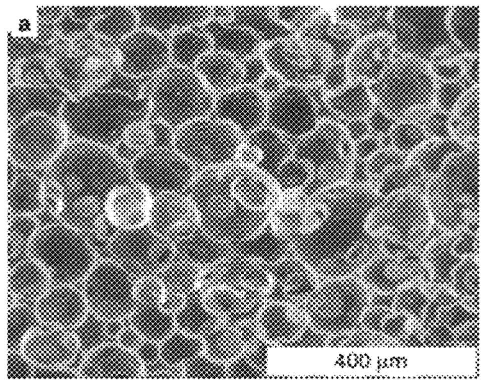
Figure 4B:
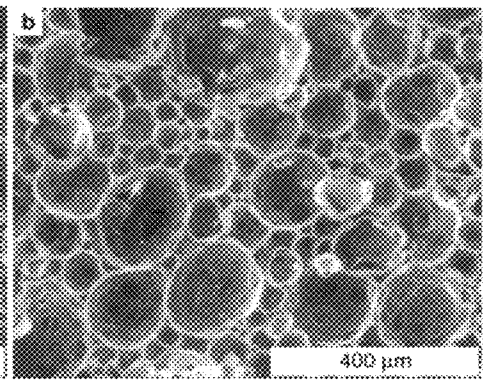
Figure 5A:
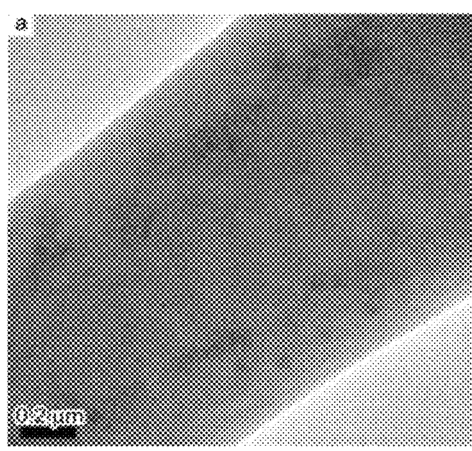
Figure 5B:
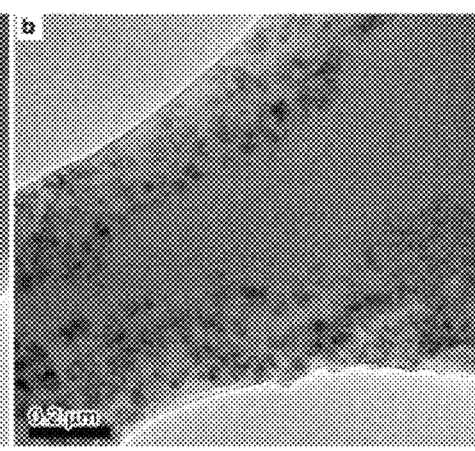
Figure 7:
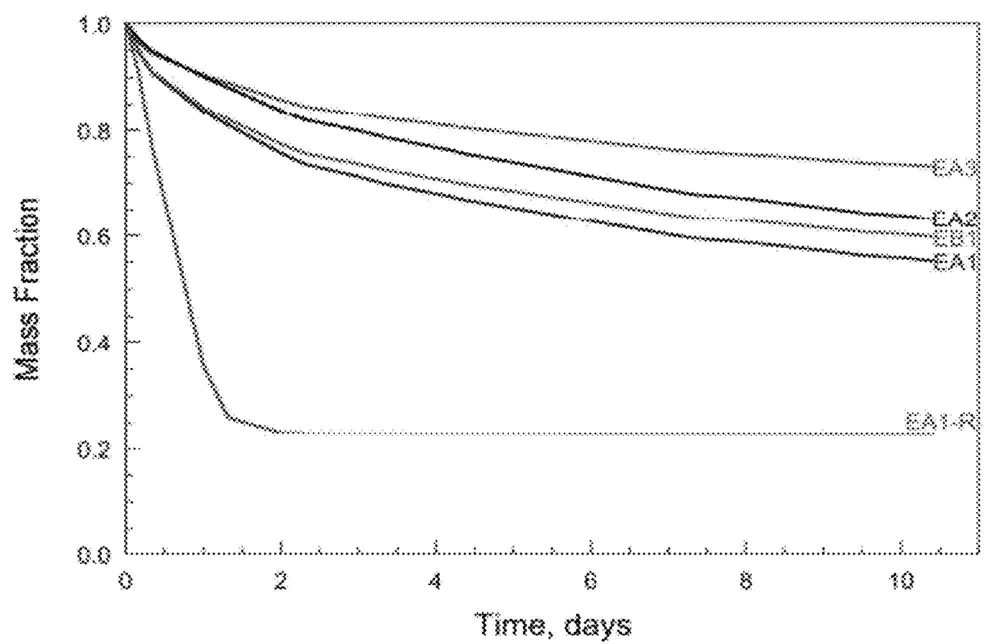
Figure 8:
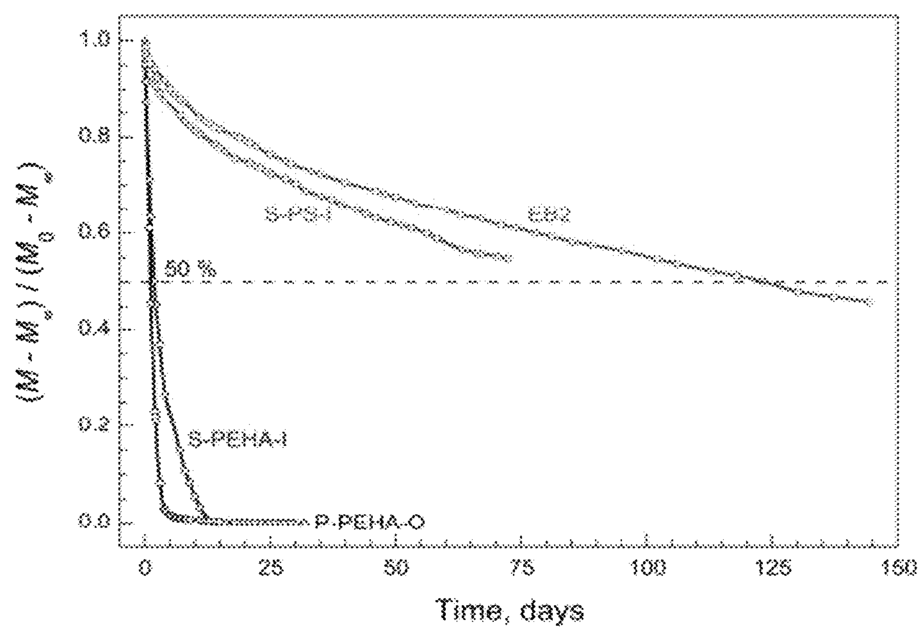

FIG. 1 presents comparative FTIR spectra of as-received silica nanoparticles (black line) A-type (red line) and B-type (blue line) MSiNPs;

FIG. 2 presents comparative plots showing the thermogravimetric mass loss (mass as a function of temperature) obtained for a sample of as-received silica nanoparticles, compared with the results obtained for samples of the A-, B- and C-type MSiNPs, conducted at a temperature range from room temperature to 800° C.;

FIGS. 3A-E are SEM micrographs of cross-sections of exemplary LDE samples EA1 (FIG. 3A), EB1 (FIG. 3B), EA3 (FIG. 3C), EA2 (FIG. 3D) and ED1 (FIG. 3E), according to some embodiments of the present invention;

FIGS. 4A-B are SEM micrographs of cross-sections of exemplary non-LDE samples EA1-R (FIG. 4A) and EB1-R (FIG. 4B);

FIGS. 5A-B are TEM micrographs of cross-sections of the walls of exemplary LDE samples EA1 (FIG. 5A) and EC1 (FIG. 5B), according to some embodiments of the present invention, showing surface modified silica nanoparticles within the walls of the LDEs;

FIGS. 6A-B presents comparative plots of the compressive stress-strain curves as measured for exemplary LDEs, according to some embodiments of the present invention, and from dried polyHIPEs with molecularly identical elastomer compositions, derived from Pickering HIPE formulations containing A-type (FIG. 6A) and B-type (FIG. 6B) MSiNPs;

FIG. 7 presents a comparative plot showing the mass loss during drying in a standard fume hood, following the exemplary LDE, according to some embodiments of the present invention, and non-LDE samples EA1, EA1-R, EA2, EA3, and EB1; and FIG. 8 presents the results of the mass loss experiments in a comparative plot showing the mass of water in the sample ($M-M_\infty$) normalized by the mass of water in the original sample ($M_0-M_\infty$) as a function of drying time for a series of tested polyHIPEs (the horizontal dotted line indicates 50% water loss).

DESCRIPTION OF SPECIFIC EMBODIMENTS OF THE INVENTION

The present invention, in some embodiments thereof, relates to polymeric material science and, more particularly, but not exclusively, to HIPE-derived liquid-retaining elastomeric compositions.

The principles and operation of some embodiments of the present invention may be better understood with reference to the figures and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

As known in the art and presented hereinabove, High Internal Phase Emulsions (HIPEs) are concentrated systems of water-in-oil, oil-in-water, or oil-in-oil possessing a large volume of internal, or dispersed phase, with a volume fraction of over 0.74, resulting in deformation of the dispersed phase droplets into polyhedra or in the formation of a polydisperse droplet size distribution. The dispersed droplets are separated by thin films of continuous phase. As HIPEs are intrinsically unstable, the HIPE is typically stabilized by adding an emulsion stabilizer to either the internal phase and/or the external phase. The HIPE structure, which is analogous to a conventional gas-liquid foam of low liquid content, gives rise to a number of properties including high viscosities and viscoelastic rheological behavior Like dilute emulsions, HIPEs are both kinetically and thermodynamically unstable; nevertheless, it is possible to prepare metastable systems which show no change in properties or appearance over long periods of time.

As discussed hereinabove, polymer materials can be prepared from HIPEs if one or the other (or both) phases of the emulsion contain polymerizable monomeric species. This process yields a range of foam-like products with widely differing properties. As the concentrated emulsion acts as a scaffold or template, the microstructure of the resultant material is determined largely by the emulsion structure immediately prior to polymerization and through changes that can occur during polymerization and/or during post-polymerization processing.

In a previous study [Gurevitch, I.; Silverstein, M. S., *J. Polym. Sci. A: Polym. Chem.,* 2010, 48, 1516-1525], the present inventors reported the synthesis of rubbery crosslinked polyacrylate polyHIPEs based on Pickering HIPEs that were stabilized using silane-modified silica nanoparticles. In that study, the nanoparticles were found to form shells around the droplets of the aqueous phase and stabilize the two-phase structure. Although appearing to inherit the microstructure of the HIPE, these polyHIPEs were found to have an open-cell microstructure, hence the liquid internal phase could not be retained in the polyHIPEs for extended periods of time.

While conceiving the present invention, the inventors have contemplated forming an elastomeric polyHIPE wherein the internal phase cannot be removed from the elastomeric matrix; hence forming an elastomer with liquid droplets entrapped therein, or in short, a liquid droplet elastomer (LDE). An LDE can also be described as a mass of an elastomeric substance filled with discrete droplets of liquid.

Without being bound by any particular theory, it was hypothesized by the present inventors that in order to arrive at a closed-cell polyHIPE that can retain the liquid part of the emulsion entrapped inside the closed-cell, the polymerizable external phase should be polymerized first at the interface between the external and the internal phases (hereinafter "the interface"), affording intact walls that engulf the internal phase droplets entirely. It was further hypothesized that two factors contribute to the formation of intact walls, locus of initiation of polymerization (hereinafter "initiation") and locus of the crosslinking hub. Crosslinks link one polymer chain to another by covalent bonds, coordinative bonds or ionic bonds. When the term "crosslinking" is used in the synthetic polymer science field, it usually refers to the use of crosslinks to promote a difference in the polymer's physical properties. The present inventors contemplated that the chemical moieties that govern crosslinking and the initiation should be located at or near the interface. The conjecture of the present inventors was that suitable conditions can be afforded by, for example, modifying the emulsion-stabilizing nanoparticles to act as both the crosslinking hub and the center of the initiation, or by modifying the emulsion stabilizers, which typically reside at the interface, to act as the crosslinking agent (crosslinking hubs) and use an aqueous-based polymerization initiator which will effect initiation at the interface, where it can come in contact with the unpolymerized mixture (monomers) constituting the external phase.

As a demonstrative example, the present inventors have now uncovered that manipulating the locus of initiation while using Pickering HIPEs stabilized with modified silica nanoparticles, one can afford polyHIPEs exhibiting a close-cell microstructure. Specifically, it was observed that when using silica nanoparticles which have been modified so as to bear polymerizable moieties on their surface, and using polymerization initiators which act within the organic polymerizable external phase, one obtains open-cell polyHIPE structures. However, if the polymerization initiator is acting from within the aqueous internal phase, closed-cell polyHIPE structures are obtained, such that retain the internal phase entrapped therein for exceedingly long period of time.

It was further uncovered that closed-cell polyHIPEs can also be obtained when the locus of the initiation center is placed on the surface of the emulsion stabilizing nanoparticles instead of in the internal phase.

The present inventors have practiced and demonstrated the above by using inorganic nanoparticles that were modified so as to have dual functionality: (i) to stabilize the Pickering HIPE, and (ii) to bear a plurality of propyl-methacrylate moieties on their surface; and further by using an aqueous soluble initiator. This demonstrative example afforded a liquid droplet elastomer, as this phrase is defined herein.

The present inventors have further practiced and demonstrated the above by using inorganic nanoparticles that were further modified so as to have a triple functionality: (i) to stabilize the Pickering HIPE, (ii) to bear a plurality of propyl-methacrylate moieties on their surface, and (iii) to bear an initiator moiety on their surface, such as an activator generated by electron transfer atom transfer radical polymerization initiator, typically abbreviated as AGET-ATRP. This demonstrative example also afforded a liquid droplet elastomer.

Thus, the present inventors have successfully designed and produced novel compositions-of-matter, which are referred to herein as liquid droplet elastomers.

As used herein, the phrase "liquid droplet elastomer", also referred to herein as LDE, describes a monolithic composition-of-matter comprising an elastomer and a liquid, wherein the liquid is dispersed in the elastomer in the form of a plurality of droplets or cavities/cells entrapping the liquid, also referred to herein a closed-cell microstructure. Hence, the liquid droplets in an LDE can be described as a closed liquid-filled cavities or closed cells of liquid. In the context of embodiments of the present invention, the droplets in an LDE are not interconnected, hence the liquid which is entrapped in the LDE cannot escape, and liquid loss from an LDE is essentially limited to the rate of diffusion of the liquid through the walls of the elastomer. In the context of embodiments of the present invention, the liquid droplets are dispersed substantially evenly throughout the bulk of the elastomer.

Hence, according to one aspect of embodiments of the present invention, there is provided a process of preparing a composition-of-matter which includes a continuous elastomeric matrix and a liquid dispersed throughout the matrix and entrapped therein in a form of a plurality of droplets (also referred to herein as an LDE). The process is effected by forming a HIPE by using any general or particular method known in the art for forming HIPEs with a polymerizable external phase, and subjecting the polymerizable external phase to initiation and effecting crosslinking substantially at the interface.

By subjecting the polymerizable external phase to initiation it is meant that both the initiation and the crosslinking of polymer chains in the polymerizable external phase are effected substantially at the interface between the phases. As the processes of polymerization and crosslinking are essentially simultaneous, it can be said that among other manners, an LDE is afforded when the initiation and the crosslinking of the emerging polymeric chains is effected essentially simultaneously and at essentially the location where the internal phase is in contact with the external phase. Affording initiation and crosslinking essentially at the interface, rather than anywhere in the bulk of any of the phases, is referred to herein as "concerted control of loci".

As demonstrated herein, such a concerted control of loci is afforded by one or a combination of the following exemplary methods:

(i) using emulsion stabilizers, which are inherently located at the interface, and which can also serve as crosslinking agents (hence dual functionality), and using an initiator which is soluble in the internal phase; and/or (ii) using emulsion stabilizers that can also serve as crosslinking agents as well as initiators (hence triple functionality).

The microstructure of the composition-of-matter obtained by the described process is derived from the structure of the HIPE. According to some embodiments of the present invention, the HIPE has an aqueous internal phase and an organic polymerizable external phase.

According to some embodiments of the present invention, the ratio of the organic polymerizable external phase to the aqueous internal phase in such a HIPE ranges from 0.05 to 0.67. Alternatively it can be said that the mass ratio of polymerizable external phase to the aqueous internal phase ranges from 5 to 95 (5:95) to 4:6 parts, respectively. Further alternatively it can be said that the mass of the internal phase constitutes from 60% to 95% of the total mass of the HIPE.

HIPE can be stabilized with emulsion stabilizers which can include organic (e.g., polyoxyethylene glycol alkyl ethers) and inorganic (e.g., polyphosphates) surfactants and, in the case of Pickering HIPE, inorganic or organic particles. Exemplary emulsion stabilizers that are suitable for use in the context of some embodiments of the invention include, without limitation, surfactants such as the Span family of surfactants (such as sorbitan monooleate (SMO), sorbitan monolaurate (SML)), olyglycerol polyricinoleate (PGPR), and the Hypermer family of surfactants, which are all usually used for w/o HIPEs, as well as the Tween family of surfactants, the Triton family of surfactants, sodium lauryl sulfate (SLS), sodium dodecyl sulfate (SDS), which are all usually used for o/w HIPEs, and, in addition block copolymers such as PEO-PPO-PEO and the likes, any organic and inorganic particles, unmodified or modified, such as, for a non-limiting example, metal oxide or semi-metal oxide particles, silica particles, modified silica particles, titania particles, zirconia particles, alumina particles, carbon black particles and carbon nanotubes.

According to some embodiments of the present invention, the HIPE used to produce the composition-of-matter presented herein is a Pickering HIPE, namely a HIPE which is afforded and stabilized by use of particles. Pickering emulsions can be made with nanometer-sized, micrometer-sized particles or millimeter-sized particles. The particles can be inorganic (metals, semiconductors, oxides, carbides, nitrides, sulfides, etc.) or organic (polymers insoluble in both phases, crosslinked polymers that can swell but not dissolve). The particles could be of any shape.

According to some embodiments of the present invention, the emulsion stabilizer is in the form of a plurality of silica nanoparticles, and more specifically, a plurality of silica nanoparticles having their surface modified so as to possess the additional functionalities discussed herein and demonstrated in the Examples section that follows.

As used herein, the term "nanoparticle" describes one or more nano-sized discrete mass of solid particles being less than 100 nm in the smallest axis thereof.

The nanoparticles, according to some embodiments of the present invention, have an average particle diameter less than about 100 nm, less than about 50 nm, less than about 20 nm, less than about 10 nm, less than about 5 nm and even less than about 1 nm. In some embodiments, the nanoparticles have an average particle diameter in the range of, for example, 0.1-100 nm, 0.1-50 nm, 0.1-20 nm, 0.1-10 nm or 5-10 nm.

The nanoparticle are generally members of a population having a narrow size distribution and a general shape of a sphere, a cube, a box, a rod, a disk, a tripod, a tetrapod and the like.

According to some embodiments of the present invention, the nanoparticles are inorganic nanoparticles which are suspendable in liquid media and can stabilize a HIPE, namely capable of forming Pickering HIPE compositions. As noted hereinabove, HIPEs can be stabilized with nanometer-sized particles to millimeter-sized particles, hence the description of surface modification of the particles applies to particles of all sizes.

The additional functionalities are added to the nanoparticles by surface modifications, affording modified particles or nanoparticles. The phrases "modified particles", "modified nanoparticles" and any particular examples thereof, such as "modified silica nanoparticles", refer to particles or nanoparticles which have been treated by one or more chemical reactions so as to modify the chemistry of their surface (surface-modified nanoparticles), thereby bestowing chemical reactivity to the nanoparticles which was not present in the parent nanoparticles. In general, when referring to inorganic nanoparticles in the context an emulsion stabilizer of Pickering HIPE, according to embodiments of the present invention, it is meant to encompass a plurality of fully modified, partially modified and un-modified nanoparticles, unless one is specifically excluded.

As used herein, the phrases "associate with", "associating with" and "attached to" encompass covalent bonding, hydrogen bonding, electrostatic attraction, London forces, and hydrophobic interactions.

The surface chemistry of the particles can be modified by any method or process known in the art, such as etching by acid, base, plasma or radiation. In the context of the present embodiments, a nanoparticle is modified by way of grafting, namely covalently attaching a plurality of chemical moieties thereto by reacting one or more surface-modifying agents with reactive surface groups which are found on the surface of the nanoparticle. For instance, a surface modifying and polymerizable agent exhibiting a vinyl group thereon, can be grafted on the nanoparticle by reacting the same with reactive surface hydroxyl groups such that a plurality of polymerizable vinyl moieties is now covalently attached to its surface, thereby modifying the nanoparticle to act as a crosslinking agent. Similarly, a polymerization initiator agent (hereinafter "initiator" or "initiation agent") can be grafted onto the surface of the nanoparticle so as to modify the nanoparticle into an initiation agent due to a plurality of initiation moieties now found on its surface.

The type of available reactive surface groups depends on the particular nanoparticle and the process of its manufacturing. Surface groups typically affect the interfacial tension of the nanoparticle in a given media. Typical reactive surface groups include, without limitation, hydroxyl groups, carbonyls, thiols, amines and the likes.

The term "moiety", as used herein, refers to a part of a molecule that possesses a particular structure of functionality.

A molecule possessing such functionality can be attached to another chemical entity, thereby bestowing, at least to some extent, the same functionality to the chemical entity. Thus, in the context of the present invention, the term "moiety" refers to the active portion of a corresponding agent, while "active" refers to the relevant activity of the agent, which is appended to the term "moiety". In the context of the surface-modified nanoparticles, the surface of the nanoparticle is modified by having "modifying moieties" attached to its surface, hence surface modifying moieties. The surface modifying moieties stem from reacting surface-modifying agents with the nanoparticle via its surface reactive groups. Exemplary modifying moieties include, without limitation, polymerizable moieties and initiation moieties, as defined hereinbelow.

Surface modifying moieties are derived from their corresponding surface modifying agents, which are also known in the art as coupling agents. Schematically, a surface modifying or coupling agent can be represented by the formula A-B, where the A-moiety is capable of attaching to the surface of a particle and the B-moiety is a surface modifying moiety.

Suitable classes of surface modifying agents include, e.g., silanes, organic acids, organic bases, thiols and alcohols.

For example, alkoxysilanes having the general structure $(R_1)_{4-n}$—Si—$(OR_2)_n$, where n=1, 2, or 3, and chlorosilanes having the general structure $(R_1)_{4-n}$—Si—$Cl_n$, where n=1, 2, or 3, can be regarded as surface modifying or coupling agents represented by the formula A-B, where the Si—$(OR_2)_n$ or Si—$Cl_n$ reacts with the surface of the silica particle, and the $R_1$ modifies the nature of the surface. Non-limiting examples of useful A-B type silanes include organosilanes such as alkylchlorosilanes, alkoxysilanes, methyltrimethoxysilane, methyltriethoxysilane, ethyltrimethoxysilane, ethyltriethoxysilane, n-propyltrimethoxysilane, n-propyltriethoxysilane, i-propyltrimethoxysilane, i-prop yltriethoxysilane, butyltri methoxysilane, butyltriethoxysilane, hexyltrimethoxysilane, octyltrimethoxysilane, 3-mercaptopropyltrimethoxysilane, n-octyltriethoxysilane, phenyltriethoxysilane, polytriethoxysilane, vinyltrimethoxysilane, vinyldimethylethoxysilane, vinylmethyldiacetoxysilane, vinylmethyldiethoxysilane, vinyltriacetoxysilane, vinyltriethoxysilane, vinyltriisopropoxysilane, vinyltrimethoxysilane, vinyltriphenoxysilane, vinyltri(t-butoxy)silane, vinyltris(isobutoxy)silane, vinyltris (isopropenoxy)silane and vinyltris(2-methoxyethoxy)silane; trialkoxyarylsilanes; isooctyltrimethoxy-silane; N-(3-triethoxysilylpropyl)methoxyethoxyethoxy ethyl carbamate; N-(3-triethoxysilylpropyl)methoxyethoxyethoxyethyl carbamate; silane functional (meth)acrylates such as 3-(methacryloyloxy)propyltrimethoxysilane, 3-acryloyloxypropyltrimethoxysilane, 3-(methacryloyloxy)propyltriethoxysilane, 3-(methacryloyloxy)propylmethyldimethoxy silane, 3-(acryloyloxypropyl)methyldimethoxysilane, 3-(methacryloyloxy)propyldimethylethoxysilane, 3-(methacryloyloxy) methyltriethoxysilane, 3-(methacryloyloxy)methyltrimethoxysilane, 3-(methacryloyloxy)propyldimethyl ethoxysilane, 3-(methacryloyloxy)propenyltrimethoxysilane, 3-(methacryloyloxy)propyltrimethoxysilane; polydialkylsiloxanes such as polydimethylsiloxane; arylsilanes such as substituted and unsubstituted arylsilanes; alkylsilanes such as substituted and unsubstituted alkyl silanes, methoxy and hydroxy substituted alkyl silanes, and combinations thereof.

Methods of surface-modifying silica particles using silane functional (meth)acrylates are described, for example, in U.S. Pat. Nos. 4,491,508, 4,455,205, 4,478,876, 4,486,504 and 5,258,225, which are incorporated herein.

Useful organic acid surface-modifying agents include, without limitation, oxyacids of carbon (e.g., carboxylic acid), sulfur and phosphorus, and combinations thereof.

Representative examples of polar surface modifying agents having carboxylic acid functionality include $CH_3O(CH_2CH_2O)_2CH_2COOH$ (MEEAA) and 2-(2-methoxyethoxy)acetic acid having the chemical structure $CH_3OCH_2CH_2OCH_2COOH$ (hereafter MEAA) and mono (polyethylene glycol) succinate.

Representative examples of non-polar surface modifying agents having carboxylic acid functionality include octanoic acid, dodecanoic acid and oleic acid.

Examples of suitable phosphorus containing acids include phosphonic acids including, e.g., octylphosphonic acid, laurylphosphonic acid, decylphosphonic acid, dodecylphosphonic acid and octadecylphosphonic acid.

Useful organic base surface modifying agents include, e.g., alkylamines including, e.g., octylamine, decylamine, dodecylamine and octadecylamine.

Examples of other useful non-silane surface modifying agents include acrylic acid, methacrylic acid, beta-carboxyethyl acrylate, mono-2-(methacryloyloxyethyl)succinate, and combinations thereof.

Examples of suitable surface modifying alcohols include, e.g., aliphatic alcohols including, e.g., octadecyl, dodecyl, lauryl and furfuryl alcohol, alicyclic alcohols including, e.g., cyclohexanol, and aromatic alcohols including, e.g., phenol and benzyl alcohol, and combinations thereof.

When the nanoparticle is made of organic substance, it may exhibit a wide variety of reactive surface groups, such as, for a non-limiting example, epoxy groups.

As discussed hereinabove, according to some embodiments the nanoparticles are inorganic such as silica, zirconia, titania, ceria, alumina, iron oxide, vanadia, antimony oxide, tin oxide, alumina/silica, and combinations thereof.

Useful surface modified silica nanoparticles include silica nanoparticles surface modified with silane surface modifying agents including, e.g., acryloyloxypropyl trimethoxysilane, 3-methacryloyloxypropyltrimethoxysilane, 3-mercaptopropyltrimethoxysilane, n-octyltrimethoxysilane, isooctyltrimethoxysilane, and combinations thereof. Silica nanoparticles can be treated with a number of surface modifying agents including, e.g., alcohol, organosilane including, e.g., alkyltrichlorosilanes, trialkoxyarylsilanes, trialkoxy(alkyl) silanes and combinations thereof and organotitanates and mixtures thereof.

Useful surface modified zirconia nanoparticles include a combination of oleic acid and acrylic acid adsorbed onto the surface of the particle.

Exemplary methods of surface modifying organic particles are disclosed, for example, in U.S. Pat. No. 5,648,407 which is incorporated herein. Other useful surface modification processes and surface modified particles are described in, for example, U.S. Pat. Nos. 2,801,185, 4,522,958, 6,586,483, 7,129,277 and 7,189,768, which are incorporated herein.

The amount of modified nanoparticles controls several structural properties of the composition-of-matter. The concentration of the modified nanoparticles can be measure in relation to the amount of the phase in it mixed into, which can be either the internal or the external phase.

Hence, according to some embodiments of the present invention, the concentration of said modified silica nanoparticles ranges from 0.01% to 10% of the total weight of said organic external phase.

According to some embodiments of the present invention, the modified silica nanoparticles have a plurality of polymerizable moieties attached thereon, thereby transforming the nanoparticle into a crosslinking agent. A crosslinking agent is typically characterized according to its capacity to alter the rigidity of a polymeric composition. Thus, a crosslinking agent (or moiety) is a component having an effect on controlling flexibility of the obtained elastomeric matrix, giving it the desired mechanical properties. In the context of the present embodiments, the location and nature of the crosslinking agent also controls the formation of a closed- versus open-cell microstructure. In the context of the crosslinking function, a crosslinking moiety is equivalent to a crosslinking agent.

As used herein, the phrases "crosslinking agent" refers to a substance that promotes or regulates intermolecular covalent, ionic, hydrophobic or other form of bonding between polymer chains, linking them together to create a network of chains which result in a more rigid structure. Crosslinking agents, monomers or nanoparticles having a plurality of polymerizable moieties attached thereon, according to some embodiments of the present invention, contain a functionality greater than two, for example, two double bonds (vinyls) (a functionality of four) or three amines (a functionality of three), creating chemical bonds between two or more polymer molecules (chains).

In the context of multi-functional modified nanoparticles, according to some embodiments of the present invention, each individual nanoparticle which has been modified to bear a plurality of moieties that can participate in the chain-growth polymerization reaction as would other monomers, is in essence a crosslinking agent that serves as a crosslinking hub. Since any one of the plurality of polymerizable moieties attached to the nanoparticle is capable of becoming a member of a polymeric chain, the nanoparticle itself is the hub for all the polymeric chains that emanate therefrom.

Surface modifying moieties (B-moiety) which can be used for transforming nanoparticles into crosslinking agents may be monomers having a vinyl ester moiety, including the alkyl acrylates such as methyl acrylate, the alkyl maleates such as methyl maleate, the alkyl fumarates such as ethyl fumarate, the vinyl ethers such as methyl vinyl ether, the alkyl methacrylates such as ethyl methacrylate and the alkyl itaconates such as ethyl itaconate.

Collectively, monomers useful for use as polymerizable moieties according to some embodiments of the present invention, may be represented as being a monomer containing a vinyl group (e.g., ethylene, propylene, vinyl chloride, vinyl acetate, acrylates, methacrylates, styrenes, dienes) or a vinylidene group having the structural formula $CH_2{=}C<$ where at least one of the disconnected valences is attached to an electronegative radical such as phenyl, acetoxy, carboxy, carbonitrile and halogen, examples of the monomers being those hereinbefore listed as well as styrene, vinylnaphthalene, alphamethylstyrene, dichlorostyrenes, alpha-methylene carboxylic acids, their esters, nitriles and amides including acrylic acid, acrylonitrile, acrylamide; the vinyl esters of alkanoic acids including vinyl formate, vinyl acetate, vinyl propionate, vinyl butyrate, vinyl pyridine; the alkyl vinyl ketones including methyl vinyl ketone; the conjugated diolefines including butadiene-1,3; isoprenes chloroprene, piperylene and 2,3-dimethyl-butadiene-1,3.

Additional monomers useful for use as polymerizable moieties, according to some embodiments of the present invention, include, without limitation, ring-opening monomers such as lactams, lactones, cyclic ethers and epoxides; condensation monomers such as di-carboxylic acids, di-acylhalides, diamines, di-amides, di-esters, diketones, amino-acids, polyols and the likes.

The density of the various moieties found on their surface can be quantified by the amount of modifying agent used in the preparation of the modified nanoparticles, or by the concentration of the moiety with respect to a mass unit of the nanoparticle as measured. Means of measuring the concentration of a moiety relative to the mass of a nanoparticle are given in the Examples section that follows below.

Hence, according to some embodiments of the present invention, the density, or content of the polymerizable moiety on the modified silica nanoparticles, ranges from about 0.5 mmol to about 10 mmol per 1 gram of modified silica nanoparticles.

According to some embodiments of the present invention, the modified silica nanoparticles have a plurality of polymerizable moieties attached thereon, and at the same time have a plurality of initiation moieties attached thereon. Such modified nanoparticles are referred to herein as with triple functionality, being emulsion stabilizers, crosslinking agents and polymerization initiators.

The phrase "initiation moiety", as used herein, refers to a chemical moiety that, when tethered to a carrier entity such as a molecule or a particle, can initiate polymerization of monomers. In the context of the present embodiments, the phrase "initiation moiety" includes, without limitation, an AGET-ATRP moiety such a as p-chloromethyl phenyl moiety.

In the case of using a nanoparticle-grafted initiator (an initiation moiety), such an initiator can be a part of an AGET-ATRP initiating system, as this term is known in the art. Hence, according to some embodiments of the present invention, the initiation moiety grafted on the nanoparticles, is an AGET-ATRP initiator.

Typically, the use of an AGET-ATRP initiating system requires the presence of a catalyst system and a reducing agent. Hence, according to some embodiments of the present invention, the aqueous internal phase further includes a catalyst system and a reducing agent.

As used herein, the term "catalyst" describes a compound, typically a salt or a complex of a metal such as a transition metal, which is required in catalytic amounts in order to initiate or promote a chemical reaction. The catalyst system may include a catalyst per se or, optionally, the catalyst may be used in combination with one or more of a ligand, a co-catalyst, and the likes.

Hence, according to some embodiments of the present invention, the aqueous internal phase further includes a catalyst (e.g., a transition metal-based catalyst), a ligand and a reducing agent. Exemplary AGET-ATRP initiating systems include, without limitation, p-chloromethyl phenyltrimethoxysilane as an AGET-ATRP initiator moiety, $CuCl_2$ and $CuBr_2$ as catalysts, 2,2-bipyridine as a ligand, and ascorbic acid as a reducing agent.

In the context of embodiments of the present invention, any polymerization initiation system which includes catalysts, co-catalysts and/or ligands, as these terms are known in the art, may be suitable for use in the polymerization process discussed herein. For a detailed discussion of initiation systems and examples thereof, see for example, U.S. Pat. No. 7,507,780; "Controlled/Living Radical Polymerization: Progress in ATRP", Matyjaszewski, K. (Editor), American Chemical Society; Washington, D.C., 2009; or "From mechanism and kinetics to precise ATRP synthesis", Mueller, L. A., Golas, P. and Matyjaszewski, K., "New smart materials via metal mediated macromolecular engineering", Koshravi, E., Yagci, Y., Saveleyev, Y., Eds., NATO Science Series E, Springer Science/Business Media B.V, 2009, p. 3-16.

As discussed hereinabove, another way to arrive at a closed-cell microstructure and obtain an LDE according to some embodiments of the present invention, is to use an initiator that can be mixed in the internal phase, thereby effecting initiation only at the interface between the internal phase and the polymerizable external phase. The use of an aqueous-soluble initiator may obviate the need to graft initiator moieties on the surface of the HIPE stabilizing particles. Hence, according to some embodiments of the present invention, the aqueous internal phase may include a water-soluble initiation agent.

Exemplary water-soluble initiation agents include, without limitation, water-soluble peroxides or water-soluble persulfates such as potassium persulfate (KPS) and ammonium persulfate (APS).

It is noted herein that the invention is not limited to the use of one particular polymerization mechanism, and hence not limited to any particular initiation mechanism. A variety of polymerization mechanisms including, but not limited to, chain-growth polymerization (free radical, controlled free radical, anionic, cationic and the like) and step-growth polymerization (condensation and addition and the like), ring opening polymerization, and others, are also encompassed and contemplated according to embodiments of the invention presented herein. For example, a photoinitiator can be used, and a light/radiation activated initiator can be dispersed or dissolved in the aqueous internal phase, or grafted as an initiation moiety on the surface of the emulsion stabilizing particles of a Pickering HIPE. For another example, an LDE can be formed from a HIPE which is based on polymer solutions in which evaporation of one or more constituents of the solution (e.g., solvent) is used to produce the final composition of matter, such that the solidification process is effected by loss or reduction in quantity of one or more volatile component from the HIPE.

Other reagents that can afford LDEs, according to some embodiments of the present invention, are also contemplated, including other multi-functional reagents that can serve as emulsion stabilizers and at the same time serve as crosslinking hubs, and other reagents that will have the additional function of serving as an initiation center. Such multi-functional reagents are not required to be in a form of nanoparticles, as some specially designed molecule can be synthesized to have all the aforementioned functionalities, namely a surfactant that can initiate and crosslink polymerization reactions at the interface of the internal and external phases in a HIPE.

As the polymerizable external phase is the part of the HIPE that undergoes polymerization, the organic external phase can be regarded as an unpolymerized mixture, ready to undergo an initiation event and polymerize. The polymerizable entities in the unpolymerized mixture are typically referred to as monomers. Hence, according to some embodiments of the present invention, the organic external phase is an unpolymerized mixture which includes at least one monomer characterized as forming a polymer having a tensile modulus of less than 600 MPa. Alternatively, the monomer is characterized as forming a polymer having a tensile modulus of less than 500 MPa, less than 400 MPa, less than 300 MPa, less than 200 MPa or less than 100 MPa.

Exemplary monomers useful in the context of the present embodiments include, without limitation, acrylates, methacrylates, vinyl esters, vinylidenes, lactams, lactones, cyclic ethers, epoxides, di-carboxylic acids, di-acylhalides, diamines, di-amides, di-esters, diketones, amino-acids, polyols and the likes.

Non-limiting examples of suitable monomers include various acrylates such as 2-ethylhexyl acrylate (EHA), n-butyl acrylate (nBA) and the likes.

In the context of the present embodiments, the unpolymerized mixture can be composed of more than one type of monomer (co-monomers), whereas polymerization of such mixture leads to the formation of a co-polymer. As long as the unpolymerized mixture is capable of forming a HIPE, and the resulting co-polymer is an elastomer, such an unpolymerized mixture containing such monomers is suitable for forming the composition-of-matter presented herein.

According to some embodiments of the present invention, the concentration of the monomer(s) ranges from 90% to 99.99% of the total weight of the unpolymerized mixture, corresponding to the organic polymerizable external phase.

The unpolymerized mixture may further comprise reinforcing agents, conducting agents, magnetic agents, curing agents, cure accelerators, catalysts, tackifiers, plasticizers, flame retardants, flow control agents, fillers, organic and inorganic microspheres, organic and inorganic microparticles, organic and inorganic nanoparticles, electrically conductive particles, thermally conductive particles, fibers, antistatic agents, antioxidants, anticorrosion agents, UV absorbers, colorants and other typical additives which add beneficial properties to the finished polymer.

It is noted herein that an additive can also be dispersed rather than dissolved; hence, an additive can be a solid or an immiscible liquid that is wetted or engulfed by the liquid in the organic phase and is uniformly dispersed substantially without forming agglomerates, floating or forming a sediment.

Once the polymerization process is complete, the internal phase is entrapped in the polymerized external phase in the form of a plurality of closed cells or droplets. The liquid part of the afforded composition-of-matter, according to some embodiments of the present invention, can be any organic solvent solution (typically resulting from an oil-in-water emulsion) or aqueous based solution (typically resulting from a water-in-oil emulsion), or a mixture thereof, which may contain one of more minor or major solutes, which are entrapped as well in the cells dispersed in the elastomer, as discussed herein. According to some embodiments, the entrapped liquid is an inherent residual of the predecessor internal phase in the HIPE used in the process, from which the composition-of-matter is derived. In other words, the external phase polymerized to form a continuous elastomeric matrix, as this phrase is defined hereinbelow, and the internal phase has been entrapped in the matrix in the form of liquid-entrapping cells, as this phrase is defined hereinbelow.

According to an aspect of embodiments of the present invention, there is provided a composition-of-matter obtained by the process presented herein. According to some embodiments, the composition-of-matter is characterized by a compressive modulus of less than 600 MPa and by a mass loss t½ greater than 10 days, as these terms are defined herein, and further characterized by including a continuous elastomeric matrix and a liquid dispersed in the matrix in a form of a plurality of droplets, wherein the elastomeric matrix entraps the liquid in the droplets (liquid-entrapping cells).

As used herein, the phrases "liquid-entrapping cell", "closed-cell droplet" or "droplet" for short, refers to a droplet of liquid completely surrounded by a barrier (a wall) which is impermeable to the liquid. Hence, a liquid in a closed-cell droplet is substantially entrapped therein in the sense that the liquid cannot escape from the closed-cell droplet by flow, and it does not have direct contact with any matter beyond the barrier/wall. In the context of embodiments of the present invention, a "closed-cell droplet" forms a part of a "closed-cell microstructure" as defined herein.

According to some embodiments of the present invention, the droplets have substantially either a polyhedral shape or a spheroidal shape, which is essentially a result of the action of surface tension forces pushing neighboring spheroid cells of about the same size into the most compact packing having a minimal surface area.

A polyhedral shape is a three dimensional shape with substantially flat faces and substantially straight edges. In a liquid-liquid system such as HIPE, the way that the volume content of a relatively size-wise monodispersed internal phase can be raised above 74% is through the flattening of the shape into polyhedra. Monodisperse spheres can pack to a maximum of 74% while various polyhedra can pack to 100% since there is no "left-over" space left between the packed objects. Thus, the droplets in HIPEs would be expected to be polyhedral in shape. However, if there is intense mixing, as often used in the preparation of HIPEs, a wide distribution of sizes can result and the very small droplets can fill in the empty spaces generated by the packing of the larger droplets. In the case of a wide droplet size distribution, where maximum advantage of space filling is taken in the packing of the droplets, the shape may be more spheroidal. Droplet coalescence and Ostwald ripening may also contribute to the generation of a spheroidal droplet shape.

The general shape of the closed-cell droplets in the composition-of-matter, according to some embodiments of the present invention, is derived from the shape of the droplets of the internal phase dispersed in the external phase, as in the case of soap bubbles in a mass of froth. It can be said that upon polymerization of the polymerizable external phase, the HIPE is "frozen", or locked in the general microstructure of its ancestral HIPE.

According to some embodiments of the present invention, the droplets dispersed in the elastomeric matrix, have an average diameter that ranges from 10 nm to 500 μm, or from 100 nm to 500 μm, or from 100 nm to 1 mm.

The term "spheroid", as used herein, refers to a three-dimensional characteristic of an object having the shape approximating that of a sphere, a globe or a ball, being essentially orbicular, round and globular.

The walls separating the droplets, which essentially constitute the continuous elastomeric matrix, exhibit substantially a polyhedral morphology, and a thickness that ranges from 10 nm to 500 μm, or from 10 nm to 100 μm, or from 100 nm to 1 mm.

Without being bound by any particular theory, it is noted herein that the walls fill the space between the droplets and, therefore, the cells formed by the walls take the shape of the droplets. In the LDE these often seem to be polyhedral. In surfactant-stabilized polyHIPEs with open-cell structures the cells walls formed around the droplets often seem to be spheroidal.

The droplets are dispersed substantially evenly or homogeneously throughout the volume of the elastomeric matrix. That is to say that the droplets are found in essentially similar density at any given locus in the matrix. By stating that the droplets are dispersed essentially at similar density throughout the matrix it is meant that more than 50% of the matrix exhibits a particular droplet density, or at least 70%, at least 90% or at least 99% of the matrix exhibits the same droplet density. Alternatively, it can be said that no more than 10% of the matrix exhibits a different droplet density.

One of the features that distinguish LDEs, namely the composition-of-matter presented herein, from non-LDE polyHIPEs structures, stems from the closed-cell microstructure of LDEs which is not found in presently known elastomeric polyHIPEs. According to some embodiments of the present invention, the closed-cell microstructure is afforded by the unique process presented herein for forming LDEs.

The phrase "closed-cell microstructure", as used herein, refers to the microstructure of a continuous elastomeric matrix which forms a part of the composition-of-matter according to some embodiments of the present invention. Having a plurality of intact closed-cell liquid droplets dispersed throughout the matrix, the structure of the matrix resembles that of a mass of bubbles as in soap froth, wherein each bubble shares its walls with its adjacent neighbors while remaining intact in the sense of being closed, un-punctured and substantially sealed, hence having essentially no holes in the walls. The resemblances to a mass of soap bubbles, or any other rigid or liquid closed-cell foam, ends in that the bubbles in the composition-of-matter presented herein, are filled with liquid rather than gas as in a closed-cell foam, hence these bubbles are referred to as closed-cell droplets; and further distinguishing the composition-of-matter presented herein are the un-punctured walls constituting the matrix, which is essentially a continuous mass of an elastomeric substance.

Hence, according to some embodiments of the present invention, the unique composition-of-matter afforded by a process as described hereinabove, draws its macroscopic characteristics from the materials used in the process, namely the elastomeric nature of the matrix and the chemistry and properties of the entrapped liquid; from the concerted phase interface location of the initiation and crosslinking of the external phase of the HIPE which affords the unique closed-cell microstructure; and from the closed-cell microstructure itself, which is inherited from the morphology of the HIPE it is derived from.

Thus, according to another aspect of embodiments of the present invention, there is provided a composition-of-matter which includes a continuous elastomeric matrix and a liquid dispersed throughout the matrix in a form of a plurality of droplets, wherein the elastomeric matrix entraps the liquid in the droplets, and is characterized by a compressive modulus of 600 MPa (Mega Pascal) or less, and by a mass loss $t_{1/2}$ (as defined hereinbelow) greater than 10 days.

In some embodiments, the composition-of-matter is characterized by a compressive modulus of less than 500 MPa, less than 100 MPa, less than 50 MPa, less than 10 MPa or less than 1 MPa.

The term "elastomer" and its grammatical inflections, refer to a rubber-like stretchable and flexible polymeric substance, being capable of returning substantially to its original form once the deforming force effecting stress/strain has ceased. An elastomer is typically a polymer having a relatively low tensile modulus.

The phrase "tensile modulus" refers to a physical quantity in solid mechanics, which is also known as the Young's modulus. It is a measure of the stiffness of an elastic substance, defined as the linear slope of a stress-versus-strain curve in uniaxial tension at low strains in which Hooke's Law is valid.

The phrase "compressive modulus" refers to a physical quantity in solid mechanics, which is theoretically equivalent to Young's Modulus determined from tensile experiments. It is a measure of the stiffness of an elastic substance, defined as the linear slope of a stress-versus-strain curve in uniaxial compression at low strains in which Hooke's Law is valid, hence it is the ratio of compressive stress to compressive strain below the proportional limit.

The tensile or compressive moduli, which are macroscopic properties of the composition-of-matter presented herein, can be determined experimentally from the slope of a stress-strain curve recorded during standard tensile or compression tests conducted on a sample of the composition-of-matter. In the context of embodiments of the present invention, the compressive modulus is not synonymous with the tensile modulus, the bulk modulus or the shear modulus of a substance, which refer to different elastic moduli.

As used herein, the term "continuous" refers to a macroscopic as well as a microscopic property of the elastomeric matrix forming a part of the composition-of-matter presented herein. According to some embodiments of the present invention, the elastomeric matrix is a continuous mass of the elastomer, as opposed to an assembly or aggregate of discrete bodies which are discontinuous with respect to one-another even if these are in direct contact with one-another. Hence, in the context of embodiments of the present invention, the phrase "continuous elastomeric matrix" refers to a continuous mass of an elastomeric substance.

The term "entrap" and its grammatical inflections, as used in the context of the present invention, relate to any form of accommodating a substance, herein the liquid, within a matrix, herein the continuous elastomeric matrix. As used herein, entrapment of a liquid in a continuous elastomeric matrix, as in the context of the present invention, describes complete integration of the liquid within the elastomeric matrix, such that the entrapped liquid is entirely isolated from the surrounding environment.

In the context of embodiments of the present invention, the liquid cannot escape from the elastomeric matrix by flow; however, the walls of the matrix may be permeable to some extent to some solutes and/or components of the liquid, such as molecules of the major solvent, molecules of minor co-solvents, solute molecules, dissolved gas molecules and other charged or uncharged molecular species which are capable of, at least to some degree, diffusing through the walls of the matrix. Such permeability, solubility, dissolvability or diffusivity may also be influenced by various osmotic pressures and concentration potentials. Still, the loss of mass due to evaporation of the internal phase in LDEs, according to some embodiments of the present invention, is exceedingly slow, and can be regarded as infinite when compared to open-cell polyHIPEs of the same chemical composition.

The macroscopic attribute of loss of mass of a substance can be correlated to an absolute scale, which enable the skilled artisan to compare various compositions to one another in that regard. Such a scale can be, for example, the half life, or $t_{1/2}$ of loss of mass.

In the context of embodiments of the present invention, the original mass of the composition-of-matter presented herein, $M_0$, combines the non-evaporable mass stemming mostly from the mass of the elastomeric matrix, $M_\infty$, and the original evaporable mass stemming mostly from the mass of the liquid, $(M_0-M_\infty)$. The non-evaporable mass may be derived from the original composition of the HIPE from which the polyHIPE is derived or may be determined experimentally.

In the context of embodiments of the present invention, the phrase "$t_{1/2}$ of loss of mass" refers to a macroscopic property of the composition-of-matter presented herein, which expresses its capacity to retain its evaporable mass, stemming mostly from the mass of the entrapped liquid, for exceedingly long periods of time compared to other similar compositions, e.g., where the liquid is not entrapped. This physical constant is defined as the half life time period ($t_{1/2}$) corresponding to the time period (t) in which the mass of the evaporable component of an object $(M-M_\infty)$ will reach half of its original magnitude $(M_0-M_\infty)$, namely $(M-M_\infty)/(M_0-M_\infty)=0.5$. In the context of embodiments of the present invention, this physical constant is calculated as follows:

A sample of any given composition is weighed at the beginning of the experiment to determine its initial/original mass ($M_0$). The mass of the non-evaporable component ($M_\infty$) is then calculated based upon the original composition of matter or could be determined at the end of the experiment in the event that the mass of the evaporable component has reached zero. The sample is maintained at constant environmental conditions of temperature, pressure and atmosphere, and the mass (M) is then measured at various intervals of time (t). For relatively short periods of time, the normalized mass of the evaporable component $(M-M_\infty)/(M_0-M_\infty)$ is correlated to the variable of time through the following expression:

$$\ln\left(\frac{(M-M_\infty)}{(M_0-M_\infty)}\right) = -kt; \qquad \text{Equation 1}$$

wherein k in Equation 1 is the rate constant. The rate constant can be calculated through a linear fit to the initial data in a graph of $\ln(M-M_\infty)/(M_0-M_\infty)$ versus t. The half life ($t_{1/2}$), the time for $(M-M_\infty)/(M_0-M_\infty)$ to reach 0.5, is calculated as follows:

$$t_{1/2} = -\frac{1}{k}\ln(0.5). \qquad \text{Equation 2}$$

As demonstrated in the Examples section that follows below, samples of exemplary compositions-of-matter, according to some embodiments of the present invention, exhibited exceedingly longer $t_{1/2}$ values compared to similar compositions composed of essentially the same materials and having essentially the same starting content of elastomer and liquid.

An LDE, according to embodiments of the present invention, comprises an elastomeric matrix which is reversibly deformable by definition, and a liquid which is incompressible but flowable by definition. Hence, more force (stress) is required to deform the LDE owing to the presence of the entrapped liquid within the closed-cells, which limits the deformation of the elastomer more than does the presence of empty or open-cells, which provide no resistance to deformation.

While reducing the present invention to practice, the present inventors have noticed that while open-cell polyHIPEs of similar chemical compositions can be deformed according to the inherent mechanical properties of the elastomeric substance comprising the open-cell polyHIPE, LDEs can be deformed to a much lesser extent, presumably due to the fact that the liquid-containing cells are closed. In other words, the modulus of an LDE is similar to that of an open-cell polyHIPE as the modulus is determined at low strains, reflecting the behavior of the walls at low deformations. The stress-strain curves for molecularly similar open-cell and closed-cell polyHIPEs are similar until about 30% strain. However, at 30% strain the wall of an open-cell polyHIPE can deform into the voids such that the sample becomes denser. This is not possible for the LDE since there is no empty space available. Therefore, for the LDE the stress increases more rapidly for deformations above 30%. The entire specimen deforms without changing its volume until the elastomeric walls ruptures and the closed liquid-filled cells burst, releasing the liquid and allowing more extensive deformation of the walls to take place.

According to yet another aspect of the present invention, there is provided an article-of-manufacturing which includes or is based on the LDE compositions-of-matter presented herein.

By virtue of being elastomeric and containing a considerable amount of entrapped liquid, the article-of-manufacturing can benefit from both these characteristics, and combine these in one product, typically attainable with two or more products.

For example, LDEs can be used to form stretchable isolating films, sheets, blocks or otherwise any object, that when punctured or penetrated, ooze a solution containing an active agent such as, without limitation, a drug, an antibiotic agent, a polypeptide, an antibody, a catalyst, an anticorrosion agent, a fire retardant, a sealing agent, an adhesive agent, a colorant, an odoriferous agent, a lubricant, and any combinations thereof.

The nature and optimal use of the article-of-manufacturing made from LDEs depends on the nature of the matrix and the liquid entrapped therein. Due to the ratio of liquid to matrix, the liquid being the major component of the composition-of-matter, would have a more profound influence on the practical uses thereof. For example, a liquid with high energy absorption properties, such as, for example aqueous solutions of hydroxypropyl methylcellulose and other viscoelastic liquids, will render the composition-of-matter more suitable for use in the manufacturing of an article for impact absorption. In another general example, a composition-of-matter exhibiting an entrapped solution of an active agent will be suitable for use in the manufacturing of an article wherein leakage of the solution concurrent to impact effects delivery of the solution at the location of the puncture caused by the impact.

The article-of-manufacturing can benefit from the flexibility of the elastomeric matrix and energy-absorbing and dissipating capacity of the entrapped liquid, and be used as, for non-limiting example, an energy absorption and dissipation article (insoles, bike seats cushions, carpet underlay, etc.), a vibration absorption article (motor mounts, loudspeaker mounts, etc.), a noise absorption article (quiet-room insulation, earplugs, etc.), a cushioning article, a thermal insulating article (cold/hot packs, refrigerator and air-conditioning insulation, etc.), and an impact protection article (protective sportswear, battle gear, etc.).

In cases where the liquid is an aqueous solution, LDEs can be used as dampening material, moisture and humidity control material, fire resistant material, etc.

When having a biologically active agent as a solute in the entrapped liquid, the LDEs can be used to form surgical gloves, septum seals, and other medical devices wherein a drug or a disinfectant is required upon penetration of a barrier. An exemplary use of an LDE is the manufacturing of an elastomeric glove with a sealant and colored liquid entrapped in the elastomeric matrix. Such a glove, when accidentally punctured, will provide self-sealing and breach warning functionality to the user.

It is expected that during the life of a patent maturing from this application many relevant LDEs will be developed and the scope of the term LDE is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions; illustrate the invention in a non limiting fashion.

Materials and Methods

The monomers for HIPE formation included 2-ethylhexyl acrylate (EHA) and n-butyl acrylate (nBA), obtained from Sigma-Aldrich. EHA and nBA were washed three times with a 5% by weight sodium hydroxide solution and then three times with deionized water to remove traces of any polymerization inhibitor.

Potassium persulfate (KPS, $K_2S_2O_8$), obtained from Riedel-de-Haen, was used as a water-soluble initiator.

Potassium sulfate ($K_2SO_4$), obtained from Frutarom, Israel, was added to the aqueous phase to help stabilize the HIPE (emulsion stabilization enhancer).

Benzoyl peroxide (BPO) was obtained from Fluka Chemie.

Liquid droplet elastomers (LDEs) are defined hereinabove. Non-LDE control elastomers, based on similar monomers for the polymeric matrix, were synthesized using identical Pickering HIPE procedures with the exception that the organic-soluble BPO initiator was used instead of the water-soluble initiator KPS.

Fumed silica nanoparticles having an average diameter of 7 nm and a surface area of about 390 $m^2/g$ were obtained from Sigma-Aldrich.

3-(methacryloxy)propyltrimethoxysilane (MPtMS), obtained from Alfa Aesar, was used as an alkoxysilane polymerizable coupling agent (a coupling agent containing a reactive double bond).

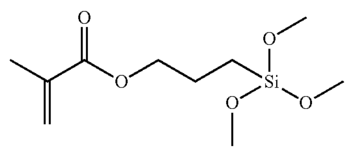

3-(methacryloxy)propyltrimethoxysilane (MPtMS)

The activators generated by electron transfer (AGET) atom transfer radical polymerization (ATRP) initiator system consisted of $CuBr_2$ (Sigma-Aldrich) as a catalyst and 2,2-bipyridine (BPY, Sigma-Aldrich) as a ligand, a reducing agent (ascorbic acid, AA, obtained from Sigma-Aldrich), and an initiator that was grafted to the silica nanoparticles (p-chloromethyl phenyltrimethoxysilane, CMPtMS, obtained from Gelest).

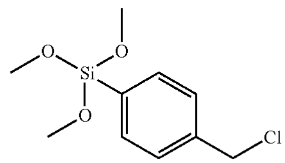

p-chloromethyl phenyltrimethoxysilane (CMPtMS)

The presence of organic groups on the nanoparticle surfaces from silane modification was characterized using FTIR from 400 to 4000 $cm^{-1}$ at a resolution of 2 $cm^{-1}$ (Equinox 55 FTIR, Bruker).

The silane-modified nanoparticles were characterized in KBr pellets containing 3% by weight sample.

The amounts of alkoxysilane incorporated on the nanoparticle surfaces were determined using thermogravimetric analysis (TGA) from room temperature to 800° C. at 20° C./min in air (2050 TGA, TA Instruments).

The molecular structures of the LDEs were characterized using photoacoustic FTIR (results not shown).

The gel content was the mass fraction that remained following immersion for 48 hours in boiling xylene and drying in a vacuum oven.

The porous structures were characterized using low vacuum scanning electron microscopy (SEM) of uncoated cryogenic fracture surfaces (FEI Quanta 200, 20 kV). The average liquid droplet (closed-cell) sizes in the LDEs and the average void (open-cell) sizes in the non-LDEs were calculated from the SEM micrographs using a correction for the statistical nature of the cross-section. LDEs were cut using cryo-ultramicrotomy and coated with a thin layer of carbon before viewing using transmission electron microscopy (TEM, FEI Technai $G^2$ T20 S-Twin, operating at 200 kV).

Compressive and tensile stress-strain measurements were carried out until displacement limitations were reached (Lloyd Tensile Machine). The moduli were determined from the initial slopes of the stress-strain curves.

The dynamic mechanical properties as a function of temperature were investigated using dynamic mechanical analysis and determine the glass transition temperature through the peak in the tan(δ) curve (DMTA, Rheometric Scientific DMTA IV).

Example I

Preparation of LDE

Modification of Silica Nanoparticle Surface with Silane:

The polyHIPE formulation that affords exemplary LDEs according to some embodiments of the present invention, utilizes silica nanoparticles as an emulsion stabilizer, stabilizing the HIPE prior to initiation. It is noted that silica nanoparticles are exemplary HIPE stabilizers and other stabilizers are contemplated in other embodiments of the present invention. The silica nanoparticles used as exemplary HIPE stabilizers have a specifically modified surface which gives the silica nanoparticles particular chemical traits which are useful in the preparation of LDEs according to some embodiments of the present invention.

Various types of modified silica nanoparticles (MSiNP) were used, and these are referred to as A-, B-, C-, or D-type MSiNPs. For all types of MSiNP an ethanol/water solution (95% by volume ethanol) and an aqueous acetic acid solution (5.5% by volume acetic acid, 1 M) were prepared. The pH of the ethanol solution was adjusted to 4.5 by adding 3% by volume of the acetic acid solution. The formulations of the reaction mixture for obtaining A-, B-, C-, or D-type MSiNPs are listed in Table 1 hereinbelow.

The alkoxysilane polymerizable agent MPtMS was grafted onto the pristine silica nanoparticles so as to produce a HIPE stabilizer with dual functionality comprising the silica nanoparticles (SiNP) and the grafted polymerizable moiety MPtMS. This HIPE stabilizer and polyHIPE crosslinking hub with dual functionality is abbreviated herein as MPtMS-MSiNP. The alkoxysilane polymerizable coupling agent MPtMS was added to a solution of ethanol, acetic acid, and deionized water at a respective ratio of 1:39.6 for A-type and 1:23.8 for B-type, and allowed to undergo hydrolysis and condensation for 1 h without stirring. The pristine silica nanoparticles were then added and stirred for 1 h. Following surface modification, the particles were filtered through filter paper and dried overnight at 70° C. to obtain MPtMS-MSiNP.

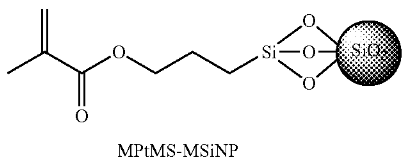

MPtMS-MSiNP

TABLE 1

| Amount, (wt %) | A-type | B-type | C-type | D-type |
|---|---|---|---|---|
| SiNP | 35.7 | 14.3 | 15.2 | 12.2 |
| MPtMS | 64.3 | 85.7 | 30.3 | 43.9 |
| CMPtMS | — | — | 54.5 | 43.9 |

The A-type MSiNP (modified silica nanoparticles) were prepared to have a relative low abundance of MPtMS polymerizable moieties on the particle's surface, hence, the A-type MSiNPs were prepared from a reaction mixture wherein the concentration of the MPtMS was 2.5% by weight relative to the solvents of the reaction mixture, and the concentration of the silica nanoparticles was 1.4% by weight relative to the solvents. For simplicity, it can be said that the ratio of MPtMS to SiNP in the A-type MSiNP is 2.5/1.4 or about 1.8.

The B-type MSiNP were prepared to have a relative high abundance of MPtMS polymerizable moieties on the particles surface, hence, the B-type MSiNPs were prepared from a reaction mixture wherein the concentration of the MPtMS was 4.2% by weight relative to the solvents of the reaction mixture, and the concentration of the silica nanoparticles was 0.7% by weight relative to the solvents. For simplicity, it can be said that the ratio of MPtMS to SiNP in the B-type MSiNP is 4.2/0.7 or about 6.

Grafting both the polymerizable MPtMS moiety and the alkoxysilane AGET-ATRP initiator p-chloromethyl phenyltrimethoxysilane (CMPtMS) moiety onto the surface of the silica nanoparticles was carried out according to the procedure described above. This grafting procedure afforded a HIPE stabilizer with triple functionality comprising a core in the form of the silica nanoparticles (SiNP), the grafted polymerizable MPtMS moiety and the grafted initiation CMPtMS moiety. This HIPE stabilizer with triple functionality is abbreviated herein as MPtMS/CMPtMS-MSiNP.

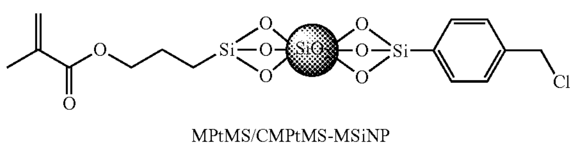

MPtMS/CMPtMS-MSiNP

The reactants used for the preparation of the C-type MSiNP included: 1.4% by weight silica nanoparticles, 2.8% by weight MPtMS and 5.0% by weight initiator p-chloromethylphenyltrimethoxysilane (CMPtMS), all relative to the weight of the solvents of the reaction mixture.

The reactants used for the preparation of the D-type MSiNP included: 1.4% by weight silica nanoparticles, 5% by weight MPtMS and 5% by weight CMPtMS, all relative to the weight of the solvents.

The ratio of MPtMS to silica was about 2.0 for the C-type and about 3.6 for the D-type. The ratio of CMPtMS to silica was about 3.6 for both the C- and the D-type.

Table 2 below presents the various reactant ratios used in the reaction mixtures during the preparation of various exemplary MSiNP-based emulsion stabilizer, according to some embodiments of the present invention:

TABLE 2

| Type | Crosslinking moiety to mass silica ratio | Initiator moiety to silica mass ratio | Total moiety to silica mass ratio |
|---|---|---|---|
| A | 1.8 | — | 1.8 |
| B | 6.0 | — | 6.0 |
| C | 2.0 | 3.6 | 5.6 |
| D | 3.6 | 3.6 | 7.2 |

FIG. 1 presents comparative FTIR spectra of as-received silica nanoparticles (black line), A-type (red line), and B-type (blue line) MSiNPs.

As can be seen in FIG. 1, the spectra indicate clearly the presence of the alkoxysilane with a narrow vinyl group band at 1630 $cm^{-1}$ in the spectrum of the A- and B-type MSiNPs.

Table 3 presents the alkoxysilane content on the A-, B-, C- and D-type MSiNP, calculated from the thermogravimetric mass loss analysis from 200 to 800° C., as presented in FIG. 2. The calculations for C- and D-type assume that the alkoxysilane ratios on the surface are the same as those used in the solution.

TABLE 3

| Type | Mass Loss, % | Content, mmol/g | Content, μmol/$m^2$ |
|---|---|---|---|
| A | 10.7 | 1.25 | 3.2 |
| B | 13.8 | 1.72 | 4.4 |
| C | 18.6 | 2.11 | 5.4 |
| D | 11.8 | 1.22 | 3.1 |

FIG. 2 presents comparative plots showing the thermograms obtained from thermogravimetric mass loss gathered from a sample of as-received silica nanoparticles, compared with the results gathered from samples of the A-, B- and C-type nanoparticles.

As can be seen in Table 3 above, the silane coverage for the A-type MSiNP is 1.25 mmol/g and increases with the increase in MPtMS content for the B-type MSiNP and with the addition of CMPtMS for the C-type. The reduction in coverage for D-type compared to C-type may indicate that CMPtMS has a higher reactivity.

LDE Synthesis—General Procedure:

The aqueous internal and the organic external phases are prepared separately, with the initiator and nanoparticles (or initiator nanoparticles) added to the appropriate phase according to each LDE formulation. For example, a water-soluble initiator such as KPS will be premixed in the internal aqueous phase, while the nanoparticles can be added to either the organic or the aqueous phase. Adding the modified silica nanoparticles to any one particular phase may affect the structure of the resulting LDE.

The internal phase content in the unpolymerized HIPE can vary from less than 60% to above 95%. Alternatively it can be said that the ratio of external to internal phase (E/I) ranges from about 0.43 to about 0.05.

The aqueous internal phase, from which the entrapped liquid is essentially derived, is prepared by mixing water, an emulsion stabilization enhancer, an optional initiation agent (initiator), and other optional components. According to some embodiments of the present invention, the emulsion stabilizer used to prepare exemplary LDEs consists of silica nanoparticles which are modified so as to exhibit additional functionalities in addition to serving as an emulsion stabilizer that stabilizes the HIPE (silica nanoparticles were added to organic external phase).

The organic external phase, from which the elastomer is essentially derived, is prepared from monomer(s) and stabilizer(s), by mixing these components into a homogenous mixture, together with any optional non-aqueous soluble or dispersible additive. According to some embodiments of the present invention, the stabilizer used to prepare exemplary LDEs consists of silica nanoparticles which are modified so as to exhibit additional functionalities in addition to serving as a HIPE stabilizer. Particles may also be added to the internal phase.

The aqueous internal phase is added to the organic external phase, containing the monomer(s), with continuous stirring. The resulting HIPE is then polymerized at a temperature that depends upon the initiator for the chain-growth reaction.

Exemplary LDE Syntheses:

The HIPE formulations used to produce the exemplary LDEs, according to some embodiments of the present invention, are listed in Table 4 below.

The header row in Table 4 presents the LDE sample codes, each consisting of two letters followed by a number. The first letter indicates the monomer used to form the elastomer, hence E for 2-ethylhexyl acrylate (EHA) and N for n-butyl acrylate (nBA). The second letter indicates the type of MSiNP used, A, B, C, or D. The number indicates a specific parameter, such as the initiator concentration or the internal phase content. Hence, EA1 is an example of a typical w/o Pickering HIPE formulation with a water-soluble initiator and 85.2% internal phase. The external phase consists of EHA (14.08% of the total weight) and A-type MSiNP (0.75% of the total weight). The internal phase consists of water (84.58% of the total weight), KPS (0.17% of the total weight), and $K_2SO_4$ (0.42% of the total weight). The variations on EA1 include a significantly higher initiator content (EA2) and a significantly higher external phase content (EA3).

The HIPE was covered with aluminum foil and polymerized in a circulating air oven at 65° C. for 24 hours without stirring.

TABLE 4

| | | Sample code | | | | | | | |
|---|---|---|---|---|---|---|---|---|---|
| | | EA1 | EA2 | EA3 | EB1 | EB2 | EC1 | ED1 | NA1 |
| External phase, % by weight | EHA | 14.08 | 13.98 | 21.92 | 14.08 | 14.06 | 14.81 | 14.81 | 0 |
| | nBA | 0 | 0 | 0 | 0 | 0 | 0 | 0 | 17.89 |
| | MSiNP | 0.75 | 0.74 | 1.16 | 0.75 | 0.74 | 0.96 | 0.96 | 0.95 |
| | $CuBr_2$ | 0 | 0 | 0 | 0 | 0 | 0.06 | 0.06 | 0 |
| | BPY | 0 | 0 | 0 | 0 | 0 | 0.04 | 0.04 | 0 |
| | Water | 0 | 0 | 0 | 0 | 0 | 0.96 | 0.96 | 0 |
| | Total | 14.83 | 14.72 | 23.08 | 14.83 | 14.80 | 16.82 | 16.82 | 18.84 |
| Internal phase, % by weight | Water | 84.58 | 83.99 | 75.99 | 84.58 | 84.43 | 83.13 | 83.13 | 80.60 |
| | KPS | 0.17 | 0.86 | 0.27 | 0.17 | 0.35 | 0 | 0 | 0.16 |
| | $K_2SO_4$ | 0.42 | 0.42 | 0.66 | 0.42 | 0.42 | 0 | 0 | 0.40 |
| | AA | 0 | 0 | 0 | 0 | 0 | 0.06 | 0.06 | 0 |
| | Total | 85.17 | 85.28 | 76.92 | 85.17 | 85.20 | 83.18 | 83.18 | 81.16 |
| E/I | ratio | 0.17 | 0.17 | 0.30 | 0.17 | 0.17 | 0.20 | 0.20 | 0.23 |

The synthesis of LDEs using AGET-ATRP initiator (EC1 and ED1) was slightly different than that for LDEs using a water-soluble initiator (KPS). The aqueous phase consisted of water and the reducing agent, ascorbic acid. A second aqueous ascorbic acid solution, identical in amount and concentration to the aqueous phase, was prepared and set aside. The BPY and $CuBr_2$ were dissolved in water before being added to the organic phase, consisting of EHA and C- or D-type MSiNP. This procedure minimized the contact between the catalyst system in the organic phase and the ascorbic acid in the aqueous phase. The organic phase was cooled in an ice bath and remained in the ice bath during HIPE formation. The aqueous phase was slowly added to the organic phase with continuous stirring. The HIPEs were covered with the second aqueous ascorbic acid solution to minimize the contact of the initiator system with air. The HIPEs were covered with aluminum foil and polymerized in a circulating air oven at 80° C. for 24 hours.

Non-LDE Syntheses:

The suffix "-R" was added to the sample codes of the non-LDEs to indicate that the liquid (water in this case) was removed from the non-LDE elastomer. The molecularly identical and structurally similar non-LDE control elastomers were synthesized following the same procedure, except that KPS was not added to the aqueous phase and, instead, benzoyl peroxide (BPO), at an amount of 1% of the monomer mass, was added to the organic phase.

Following formation of the non-LDE polyHIPE samples, the polymerized samples were placed in a freeze-dryer (Christ, Alpha 1-2 LD plus) until a constant weight was achieved. A constant mass was reached typically within 48 to 72 hours, indicating that the liquid has been substantially removed from the non-LDE polyHIPE sample.

Example 2

LDE Characterization

Chemical Characterization:

The gel content of the exemplary LDEs was determined as the mass fraction that remained following immersion for 48 hours in boiling xylene and drying in a vacuum oven.

The gel contents of 69% and 78% for EA1 and EB1, respectively, demonstrate that the MSiNP serve as crosslinking hubs for the elastomer. EB1, with its higher MPtMS content, crosslinked the elastomer more effectively.

The glass transition temperatures (Tg) for EA1, EB1, EA1-R, and EB1-R were measured at about −34° C., indicating that the molecular structures of the elastomeric walls are similar.

Visual Characterization:

As discussed hereinabove, the LDEs consist of elastomeric walls synthesized through interfacial initiated polymerization of the external phase, entrapping liquid droplets of the internal phase in evenly dispersed closed cells.

Figure 3A:
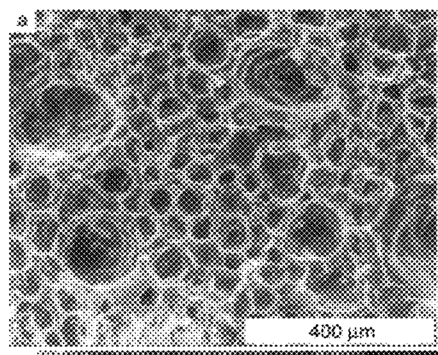
Figure 3B:
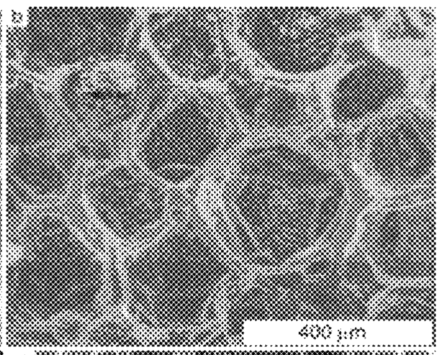
Figure 3C:
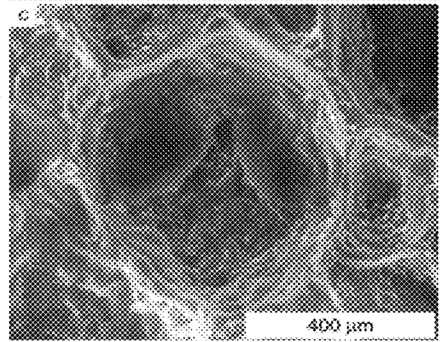
Figure 3D:
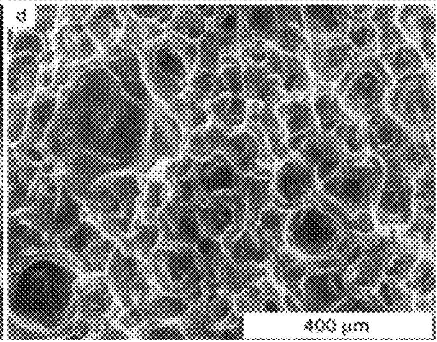
Figure 3E:
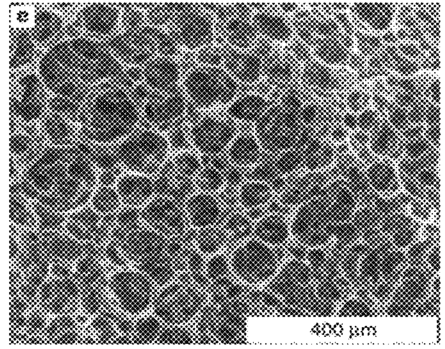

FIGS. 3A-E are SEM micrographs of cross-sections of exemplary LDE samples EA1 (FIG. 3A), EB1 (FIG. 3B), EA3 (FIG. 3C), EA2 (FIG. 3D), and ED1 (FIG. 3E).

As can be seen in FIGS. 3A-E, the dimensions of these closed cells vary from tens to hundreds of micrometers. The cryogenic fracture goes through the walls and the liquid that was entrapped evaporated when the sample returned to room temperature. The polyhedral microstructure inside the LDEs reflects the rapid polymerization at the interface that occurs when the polymerization is initiated at the interface using KPS. The rapid polymerization "locks-in" the polyhedral structure of the HIPE and forms the closed-cell structure that entraps the internal phase.

The non-LDEs consist of ruptured elastomeric walls, synthesized through polymerization initiated throughout the external phase.

FIGS. 4A-B are SEM micrographs of cross-sections of exemplary non-LDE samples EA1-R (FIG. 4A) and EB1-R (FIG. 4B).

As can be seen in FIGS. 4A-B, the spherical structures in the non-LDEs indicates that the initiation is not restricted to the interface and that allows droplet coalescence and Ostwald ripening to take place. The ruptures within the walls of the elastomer are typical of polyHIPE, and produce an interconnected, open-cell microstructure that allows the internal phase to easily flow therethrough thereby allowing the liquid to migrate and be removed.

FIGS. 5A-B are TEM micrographs of cross-sections of the elastomer wall of exemplary LDE samples EA1 (FIG. 5A) and EC1 (FIG. 5B), showing surface-modified silica nanoparticles within the elastomeric walls of the LDEs.

As can be seen in FIG. 5A, the modified silica nanoparticles are found within the wall, presumably due to the interfacial initiation, resulting from the use of a water-soluble initiator. These results shown in FIG. 5B demonstrate that nanoparticle-based initiation "locks-in" the nanoparticles at the interface, where they are located before initiation, and prevents their displacement into the wall. This distribution reflects the triple functionality of the nanoparticles, namely stabilization of the interface, initiation, and crosslinking the polymer.

Physical/Mechanical Characterization:

The LDE moduli were derived from standard compressive stress-strain analyses as presented below.

FIGS. 6A-B presents comparative plots of the compressive stress-strain curves as measured for exemplary LDEs and for dried polyHIPEs with molecularly identical elastomer compositions, derived from Pickering HIPE formulations containing A-type (FIG. 6A) and B-type (FIG. 6B) MPtMS.

The moduli of EA1 and EB1, derived from FIGS. 6A-B, are 9 and 23 kPa, respectively. The higher modulus for EB 1 reflects its higher MPtMS content which makes it a more effective crosslinking hub.

Notable and as expected, the moduli for the corresponding non-LDE are quite similar to their LDE counterparts, indicating that the elastomer dominates the mechanical properties at low strains regardless of the liquid content of the composition. The modulus derived from tensile stress-strain curves for EA1 and EB1 are similar to those derived from the compressive stress-strain curves.

The differences between the LDEs and non-LDEs at high strains in the compressive stress-strain curves presented in FIGS. 6A-B reflect the fact that the LDEs contain around 85% liquid (aqueous solution) while the dry non-LDEs contain around 85% air. The entrapped liquid within the elastomer prevents the collapse of the structure at higher deformations.

It is noted herein that the density of the exemplary LDE (closed-cell structure) demonstrated in the examples was about 1 gram per cubic centimeter, while the density of a similar polyHIPE (open-cell structure) is about 0.2 gram per cubic centimeter (open-cell structure). At high deformations such as 50%, the elastomer wall material in the open-cell polyHIPE fills the empty voids, and the density increases to about 0.4 gram per cubic centimeter. In sharp contrast, the density of an LDE stems from the elastomer (wall material) and the entrapped liquid, and since the liquid and the elastomer have densities of the same order of magnitude, there is apparently no densification in the LDE, and only deformation was recorded.

Water Retention Studies:

Water retention tests were carried out on LDE and non-LDE samples cut into small cubes of around 1 $cm^3$.

FIG. 7 presents a comparative plot showing the mass loss during drying in a standard fume hood, following the exemplary LDE and non-LDE samples EA1, EA1-R, EA2, EA3, and EB1.

As can be seen in FIG. 7, the differences between the LDEs and non-LDEs left to dry at room temperature in a fume hood are profound. The mass loss reached an asymptotic value of about 77% for the non-LDE EA1-R in less than two days, indicating that all the water has evaporated (23% of the initial mass is essentially attributed to the dry polymer), while the mass loss was only about 24% in EA1 and only 4% in EB2 during the same time period (see, FIG. 8). The rate of water evaporation is decreased by increasing the density (concentration) of the polymerizable moieties on the surface of the nanoparticles, as in the LDE sample EB1. Increasing the rate of initiation by increasing the initiator concentration, as in the LDE sample EA2, or increasing the wall thickness, as in the LDE sample EA3, reduces the rate of water evaporation.

The rate of evaporation was also monitored for more extreme conditions, in a vacuum oven at room temperature and in a convection oven at 80° C. While the water evaporates from a non-LDE in a vacuum oven within 1-2 hours, over 4 days were required for the water to evaporate from an LDE. Similarly, while the water evaporates from a non-LDE in a convection oven at 80° C. within 1-2 hours, an entire day was required for the water to evaporate from an LDE.

Video-recorded impact testing using a hammer apparatus indicated that LDEs exhibit a remarkable energy absorption mechanism which includes the release of the liquid droplets entrapped within the elastomer (results not shown).

Flammability tests demonstrated the capacity of the LDEs to retain water. While a non-LDE ignited instantly and burned furiously, an LDE based on an identical elastomer could not be ignited even when exposed directly to a butane flame.

Example 3

Analytical Mass Loss from LDE

Liquid Droplet Elastomer Mass Loss Experiments:

The loss of mass from a series of exemplary liquid droplet elastomers (LDEs), according to some embodiments of the present invention, was compared to the loss of mass from three control non-LDE polyHIPE samples. The samples were weighed at the beginning of the experiment to determine their initial mass ($M_0$). The mass of the polymer in the sample ($M_\infty$) was estimated from the feed composition. $M_\infty$, therefore, is the mass of the sample when it is essentially dry. The mass (M) was measured at various intervals of time (t). The mass of water at any time t is ($M-M_\infty$), while the initial mass of water is ($M_0-M_\infty$). The normalized mass of water [($M-M_\infty$)/($M_0-M_\infty$)] was related to the variable of time through the following expression:

$$\ln\left(\frac{(M - M_\infty)}{(M_0 - M_\infty)}\right) = -kt; \quad \text{Equation 1}$$

where k in Equation 1 is the rate constant. The rate constant can be calculated through a linear fit to the data in a graph of $\ln[(M-M_\infty)/(M_0-M_\infty)]$ as a function of time (t). The half life ($t_{1/2}$), the time for [($M-M_\infty$)/($M_0-M_\infty$)] to reach 0.5, can be determined experimentally. The half life ($t_{1/2}$) corresponds to:

$$t_{1/2} = -\frac{1}{k}\ln(0.5). \quad \text{Equation 2}$$

The LDEs and non-LDEs, jointly referred to as polyHIPEs, were based on either 2-ethylhexyl acrylate (EHA) or styrene (S) as the monomers. Some non-LDEs were stabilized with the surfactant sorbitan monooleate.

In order to gain insight on the role of the emulsion stabilizer per-se, the LDEs and some of the non-LDEs were prepared using alkoxysilane-modified silica nanoparticles as emulsion stabilizing agent.

In order to gain insight on the role of the crosslinking agent per-se, some of the non-LDEs were crosslinked with divinylbenzene (DVB), while the LDEs and other non-LDEs were crosslinked with the same alkoxysilane-modified silica nanoparticles (used to stabilize the Pickering HIPEs).

In order to gain insight on the role of the locus of initiation per-se, initiation took place either at the interface (water-soluble initiator) or on the nanoparticle surface (modified so as to act as initiator) in the case of LDEs and some non-LDEs, or within the organic phase in the case of some non-LDEs.

Preparation of the Tested polyHIPEs:

P-PEHA-1 also labeled EB2 (LDE)—an elastomeric PEHA-based polyHIPE synthesized within a Pickering HIPE through interfacial initiation. The internal aqueous phase consisted of water (84.43% of the total weight), KPS (0.35% of the total weight), and salt stabilization enhancer (0.42% of the total weight). The external organic phase consisted of EHA (14.06% of the total weight) and B-type MSiNP (0.74% of the total weight). The aqueous phase was slowly added to the organic phase with continuous overhead stirring (350-370 rpm). The HIPEs were covered with aluminum foil and polymerized in a circulating air oven at 65° C. for 24 hours without stirring.

P-PEHA-O (non-LDE)—an elastomeric PEHA-based polyHIPE synthesized within a Pickering HIPE through organic-phase initiation. The molecularly and structurally similar non-LDE control elastomer, compared to P-PEHA-I, P-PEHA-O was synthesized following the same procedure, except that KPS was not added to the aqueous phase and BPO, 0.17% by weight of the total HIPE mass, was added to the organic phase. The aqueous phase was slowly added to the organic phase with continuous overhead stirring (350-370 rpm). The HIPEs were covered with aluminum foil and polymerized in a circulating air oven at 65° C. for 24 hours without stirring.

S-PEHA-I (non-LDE)—a conventional elastomeric PEHA-based, DVB-crosslinked, surfactant-stabilized polyHIPE synthesized through interfacial initiation. The internal aqueous phase consisted of water (80.71% of the total weight), KPS (0.25% of the total weight), and salt stabilization enhancer (0.63% of the total weight). The external organic phase consisted of EHA (11.42% of the total weight), divinylbenzene (DVB Aldrich, 2.95% of the total weight) and sorbitan monooleate (SMO or Span 80, Fluka Chemie, 4.04% of the total weight). The aqueous phase was slowly added to the organic phase with continuous overhead stirring (350-370 rpm). The HIPEs were covered with aluminum foil and polymerized in a circulating air oven at 65° C. for 24 hours without stirring.

S-PS-I (non-LDE)—a rigid PS-based, DVB-crosslinked, surfactant-stabilized polyHIPE synthesized through interfacial initiation in a surfactant-poor HIPE that is known to yield a closed-cell structure. The internal aqueous phase consisted of water (78.27% of the total weight), KPS (0.34% of the total weight), and salt stabilization enhancer (0.86% of the total weight). The external organic phase consisted of styrene (S, Sigma, 9.78% of the total weight), DVB (9.78% of the total weight) and SMO (0.98% of the total weight). The amount of surfactant is extremely small, slightly less and the HIPE would not have been stable. Slightly more and an open-cell polyHIPE structure would be formed. The aqueous phase was slowly added to the organic phase with continuous overhead stirring (350-370 rpm). The HIPEs were covered with aluminum foil and polymerized in a circulating air oven at 65° C. for 24 hours without stirring.

Mass-Loss Experiments:

Mass loss tests were carried out on LDE and non-LDE samples cut into cylindrical pieces, 4.7 cm in diameter and 1.5 cm height, and total volume of 26 $cm^3$.

The cylindrical-shaped polyHIPEs were placed in a chemical hood in open Petri dishes, exposing about 4000 $mm^2$ (70%) of surface area to ambient atmosphere. The polyHIPEs were weighted (using an AND HA-200A balance) at the beginning of the experiment to determine initial mass ($M_0$), then daily for the first 30 days and then once in every 3-7 days, in order to record polyHIPE mass (M) for over 60 days.

FIG. 8 presents the results of the mass loss experiments in a comparative plot showing the mass of water in the sample ($M-M_\infty$) normalized by the mass of water in the original sample ($M_0-M_\infty$) as a function of drying time for a series of tested polyHIPEs. The mass of polymer in the sample, $M_\infty$, was estimated from the feed composition. The dotted line indicates 50% water loss.

Table 5 presents the rate constants of each of the polyHIPE samples derived from the curves presented in FIG. 8, the half life values taken from the data, as well as the mass ratios of the external phase to the internal phase (E/I).

TABLE 5

| Material | E/I | k, 1/days | $t_{1/2}$, days |
|---|---|---|---|
| LDE (P-PEHA-I) | 16/84 (0.19) | 0.00508 | 120.9 |
| S-PS-I | 22/78 (0.28) | 0.00765 | 84.1 |
| S-PEHA-I | 19/81 (0.23) | 0.275 | 2.2 |
| P-PEHA-O | 16/84 (0.19) | 0.869 | 1.2 |

As can be seen in FIG. 8 and Table 5, the polyHIPEs S-PEHA-I and P-PEHA-O, which exhibit open-cell microstructures, have very short $t_{1/2}$s of about 1 to 2 days. These non-LDEs quickly reach ($M-M_\infty$)/($M_0-M_\infty$) values of around 0%.

The polyHIPE S-PS-I sample is a representative of a rigid, non-deformable, closed-cell polyHIPE. As can be seen in Table 5, the S-PS-I polyHIPE exhibits a relatively high $t_{1/2}$ of 83.4 days.

The most remarkable results in FIG. 8 and Table 5 is the $t_{1/2}$ values of the LDE according to some embodiments of the present invention, exhibiting 120.9 days; a value which is about 50% higher than that of the rigid S-PS-I.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A composition-of-matter comprising a continuous elastomeric matrix and a liquid dispersed in said matrix in a form of a plurality of droplets, said elastomeric matrix being a polymerized external phase of a high internal phase emulsion (HIPE) and having a microstructure of said external phase and said droplets being an internal phase of said HIPE such that said elastomeric matrix entraps said liquid in said droplets, said elastomeric matrix exhibits a tensile modulus of less than 600 MPa, and further comprises a plurality of HIPE-stabilizing particles crosslinking polymeric chains of said elastomeric matrix, said HIPE-stabilizing particles being modified to exhibit a plurality of polymerizable moieties attached thereon, wherein:

said elastomeric matrix being devoid of crosslinks in a bulk thereof;

said HIPE-stabilizing particles being modified to further exhibit a plurality of initiation moieties attached thereon; and/or said elastomeric matrix further comprises a plurality of HIPE-stabilizing particles being modified to exhibit a plurality of initiation moieties attached thereon, the composition-of-matter being characterized by a compressive modulus of less than 600 MPa and by a mass loss $t_{1/2}$ greater than 10 days.

2. The composition-of-matter of claim 1, wherein said matrix is having a closed-cell microstructure.

3. The composition-of-matter of claim 1, wherein said droplets are substantially polyhedral or spheroid droplets having an average diameter that ranges from 10 nm to 500 μm.

4. The composition-of-matter of claim 3, wherein a wall separating said droplets is having a thickness that ranges from 10 nm to 500 μm.

5. The composition-of-matter of claim 1, wherein said liquid comprises at least one solute.

6. The composition-of-matter of claim 5, wherein said solute is an active agent selected from the group consisting of a drug, an antibiotic agent, a polypeptide, an antibody, a catalyst, an anticorrosion agent, a fire retardant, a sealing agent, an adhesive agent, a colorant, an odoriferous agent, a lubricant and any combination thereof.

7. A process of preparing the composition-of-matter of claim 1, the process comprising subjecting a high internal phase emulsion (HIPE), having an aqueous internal phase and an organic polymerizable external phase, to polymerization of said organic polymerizable external phase, said polymerization being initiated and effected substantially at an interface between said organic polymerizable external phase and said aqueous internal phase, wherein said organic polymerizable external phase is an unpolymerized mixture which comprises at least one monomer characterized as forming said polymer having a tensile modulus of less than 600 MPa, and wherein said aqueous internal phase and/or said organic polymerizable external phase comprises an emulsion stabilizer in the form of said plurality of HIPE-stabilizing particles.

8. The process of claim 7, wherein a mass ratio of said organic polymerizable external phase to said aqueous internal phase in said HIPE ranges from 0.05 to 0.67.

9. The process of claim 7, wherein said aqueous internal phase and/or said organic polymerizable external phase further comprises an additional emulsion stabilizer.

10. The process of claim 8, wherein said additional emulsion stabilizer is selected from the group consisting of an organic surfactant, a polyoxyethylene glycol alkyl ether, a Span, a Hypermer, a Tween, a Triton, sodium dodecyl sulfate (SDS), sodium lauryl sulfate (SLS), a block copolymer, PEO-PPO-PEO, an inorganic surfactant, a polyphosphate, a plurality of modified or unmodified particles, a plurality of modified or unmodified metal oxide or semi-metal oxide particles or nanoparticles, a plurality of modified or unmodified silica particles or nanoparticles, a plurality of modified or unmodified titania particles or nanoparticles, a plurality of modified or unmodified zirconia particles or nanoparticles, a plurality of modified or unmodified alumina particles or nanoparticles, a plurality of modified organic substance particles or nanoparticles, a plurality of modified or unmodified carbon black particles or nanoparticles, a plurality of modified carbon nanotubes, and any combination thereof.

11. The process of claim 7, wherein said plurality of modified particles is a plurality of modified silica nanoparticles having said plurality of polymerizable moieties and said initiation moieties attached thereon.

12. The process of claim 11, wherein a concentration of said modified silica nanoparticles ranges from 0.01% to 10% of the total weight of said organic polymerizable external phase.

13. The process of claim 11, wherein a content of said polymerizable moiety on said modified silica nanoparticles ranges from 0.5 mmol to 10 mmol per 1 gram of modified silica nanoparticles.

14. The process of claim 12, wherein a content of said initiation moiety on said modified silica nanoparticles ranges from 0.5 mmol to 10 mmol per 1 gram of modified silica nanoparticles.

15. The process of claim 7, wherein said aqueous internal phase further comprises a water-soluble initiation agent.

16. The process of claim 15, wherein said water-soluble initiation agent is selected from the group consisting of a water-soluble peroxide, a water-soluble persulfate, potassium persulfate (KPS) and ammonium persulfate (APS).

17. The process of claim 7, wherein said initiation moiety is selected from the group consisting of an AGET-ATRP initiator, a radical initiator, a photo-initiator and a radiation activated initiator.

18. The process of claim 17, wherein said aqueous internal phase further comprises a catalyst system and a reducing agent.

19. The process of claim 18, wherein said AGET-ATRP initiator moiety is p-chloromethyl phenyltrimethoxysilane, said catalyst system comprises CuBr2 as a catalyst, and said reducing agent is ascorbic acid.

20. The process of claim 18, wherein said aqueous internal phase further comprises a ligand.

21. The process of claim 20, wherein said ligand is 2,2-bipyridine.

22. The process of claim 7, wherein said monomer is selected from the group consisting of an acrylate, a methacrylate and a diene.

23. The process of claim 22, wherein said acrylate is selected from the group consisting of 2-ethylhexyl acrylate (EHA), n-butyl acrylate (nBA), ethyl acrylate (EA) and hexyl acrylate (HA).

24. The process of claim 22, wherein a concentration of said monomer ranges from 90% to 99.9% of the total weight of said organic polymerizable external phase.

25. The process of claim 7, wherein said unpolymerized mixture further comprises a reinforcing agent, a curing agent, a curing accelerator, a catalyst, a tackifier, a plasticizer, a flame retardant, a flow control agent, a filler, organic and inorganic microspheres, organic and inorganic microparticles, organic and inorganic nanoparticles, a conducting agent, a magnetic agent, electrically conductive particles, thermally conductive particles, fibers, an antistatic agent, a antioxidant, a anticorrosion agent, a UV absorber, a colorant and combination thereof.

26. A composition-of-matter prepared by the process of claim 7.

27. The composition-of-matter of claim 1, for use in forming an article-of-manufacture.

28. An article-of-manufacturing comprising the composition-of-matter of claim 1.

29. The article-of-manufacturing of claim 28, selected from the group consisting of an energy absorption and dissipation article, a vibration absorption article, a noise absorption article, a cushioning article, a thermal insulating article, an impact protection article, dampening material, moisture and humidity control material, fire resistant material and any combination thereof.

30. The composition-of-matter of claim 1, wherein said HIPE-stabilizing particles being selected from the group consisting of modified metal oxide or semi-metal oxide particles or nanoparticles, modified organic substance particles or nanoparticles, modified silica particles or nanoparticles, modified titania particles or nanoparticles, modified zirconia particles or nanoparticles, modified alumina particles or nanoparticles, modified carbon black particles or nanoparticles, modified carbon nanotubes and any combination thereof.

31. The composition-of-matter of claim 1, wherein said polymerizable moieties are selected from the group consisting of an acrylate, a methacrylate, a diene, an acrylamide, an acrylonitrile, an alkyl vinyl ketone, an alpha-methylene carboxylic acid, an alphamethylstyrene, an amino-acid, a butadiene-1,3, a chloroprene, a cyclic ether, a di-acylhalide, a di-amide, a diamine, a di-carboxylic acid, a dichlorostyrene, a di-ester, a diketone, a diolefine, an epoxide, an ethylene, an isoprene, a lactam, a lactone, a methyl vinyl ketone, a piperylene, a polyol, a propylene, a styrene, a vinyl, a 2,3-dimethyl-butadiene-1,3, a vinyl acetate, a vinyl butyrate, a vinyl chloride, a vinyl ester, a vinyl formate, a vinyl propionate, a vinyl pyridine, a vinylidene, a vinylnaphthalene and any combination thereof.

32. The composition-of-matter of claim 1, wherein said initiation moieties are selected from the group consisting of an AGET-ATRP initiator, a radical initiator, a photo-initiator and a radiation activated initiator.

33. The composition-of-matter of claim 1, wherein said plurality of HIPE-stabilizing particles is a plurality of modified silica nanoparticles having said plurality of polymerizable moieties and said plurality of initiation moieties attached thereon.

34. The composition-of-matter of claim 30, wherein a concentration of said modified silica nanoparticles ranges from 0.01% to 10% of the total weight of said polymerized external phase.

* * * * *